United States Patent [19]

Hudson et al.

[11] 4,017,737
[45] Apr. 12, 1977

[54] CONVEYER APPARATUS FOR MEDICAL PATIENTS

[76] Inventors: Donald C. Hudson, 502 Fenwick Drive, San Antonio, Tex. 78329; Charles R. Morris, 3119 War Arrow Drive, San Antonio, Tex. 78238; Horst G. Fleck; Karl A. Senghaas, both of 818 E. Myrtle St., San Antonio, Tex. 78212

[22] Filed: Apr. 24, 1975

[21] Appl. No.: 571,266

Related U.S. Application Data

[62] Division of Ser. No. 429,482, Jan. 2, 1974, Pat. No. 3,908,126.

[52] U.S. Cl. .............................. 250/453; 250/449
[51] Int. Cl.² ........................................ G21K 5/08
[58] Field of Search .......... 250/490, 491, 320, 453, 250/451, 456, 449

[56] References Cited

UNITED STATES PATENTS

| | | | |
|---|---|---|---|
| 3,090,865 | 5/1963 | Schneeman | 250/446 |
| 3,609,357 | 9/1971 | Jones | 250/491 |
| 3,818,516 | 6/1974 | Hopper et al. | 250/446 |

*Primary Examiner*—Archie R. Borchelt
*Assistant Examiner*—B. C. Anderson
*Attorney, Agent, or Firm*—Hubbard, Thurman, Turner & Tucker

[57] ABSTRACT

A conveyor apparatus, such as a cart, is disclosed, for aiding in the placement of subjects to be x-rayed in position in a radiographic apparatus. The conveyor apparatus includes a conveyor belt on which a patient is placed and a mechanical linkage having a mechanical advantage connecting the conveyor belt to an operator, so that relatively small movement of the operator causes relatively large movement of the patient carrying conveyor belt.

3 Claims, 31 Drawing Figures

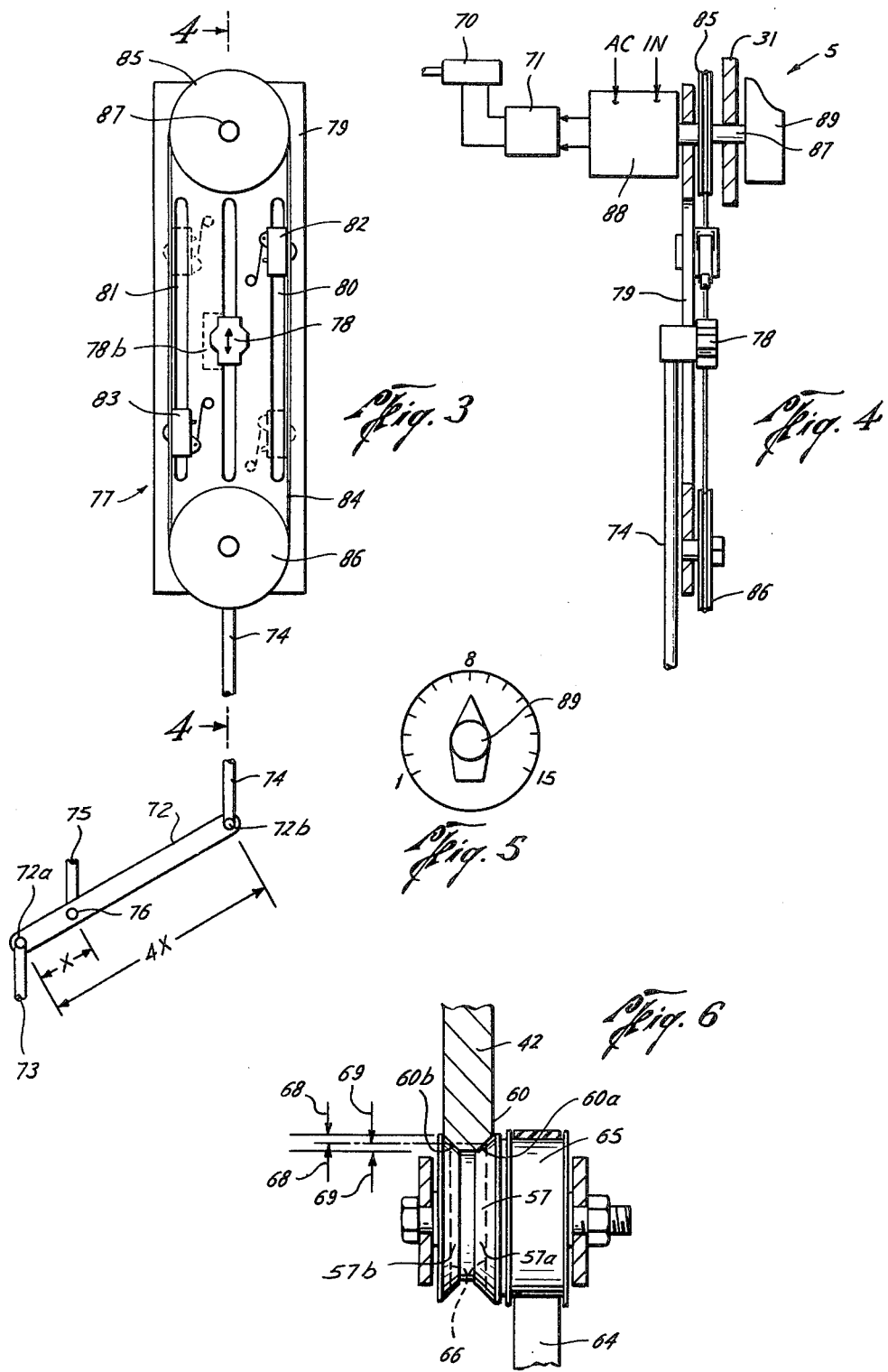

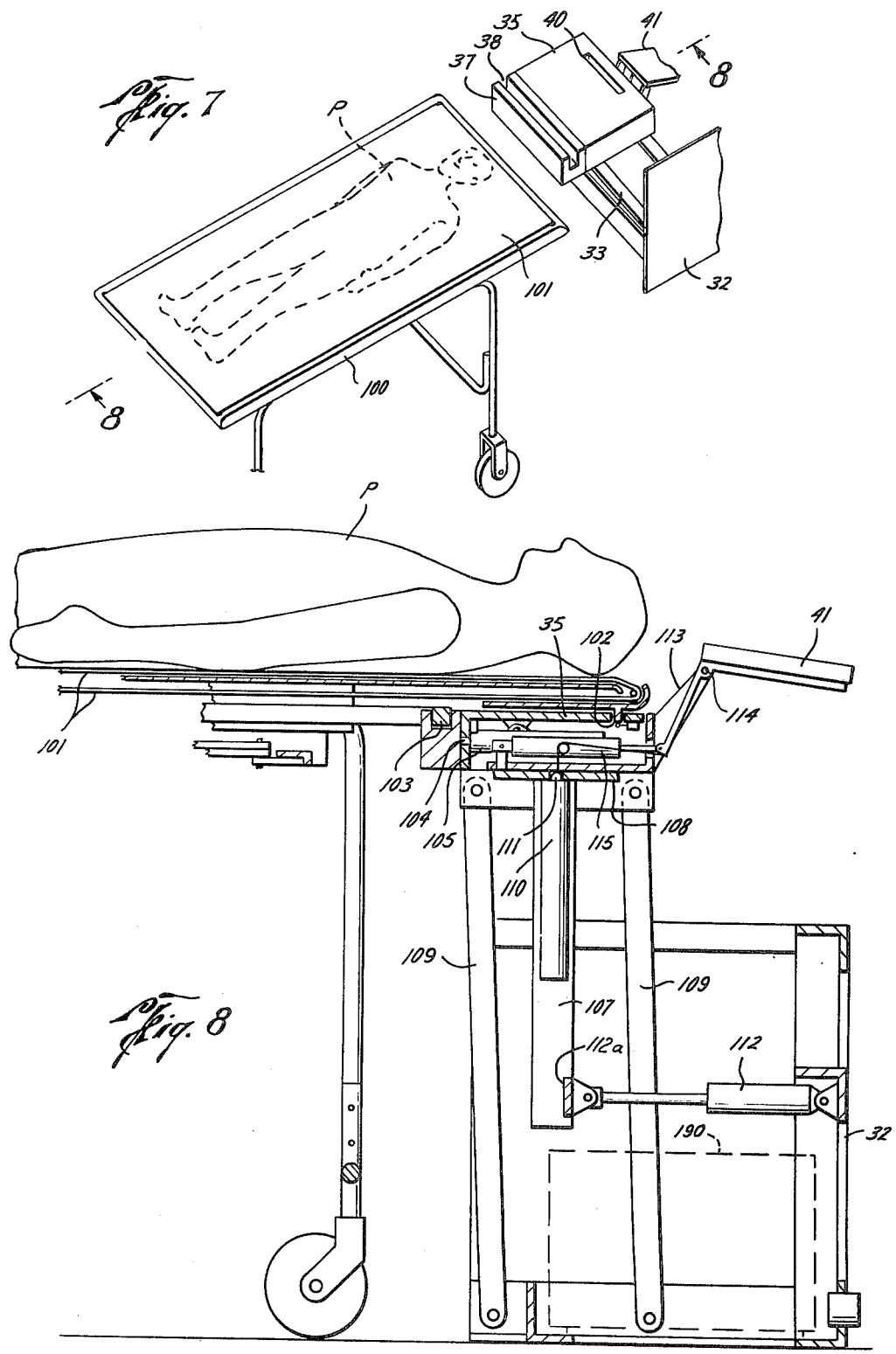

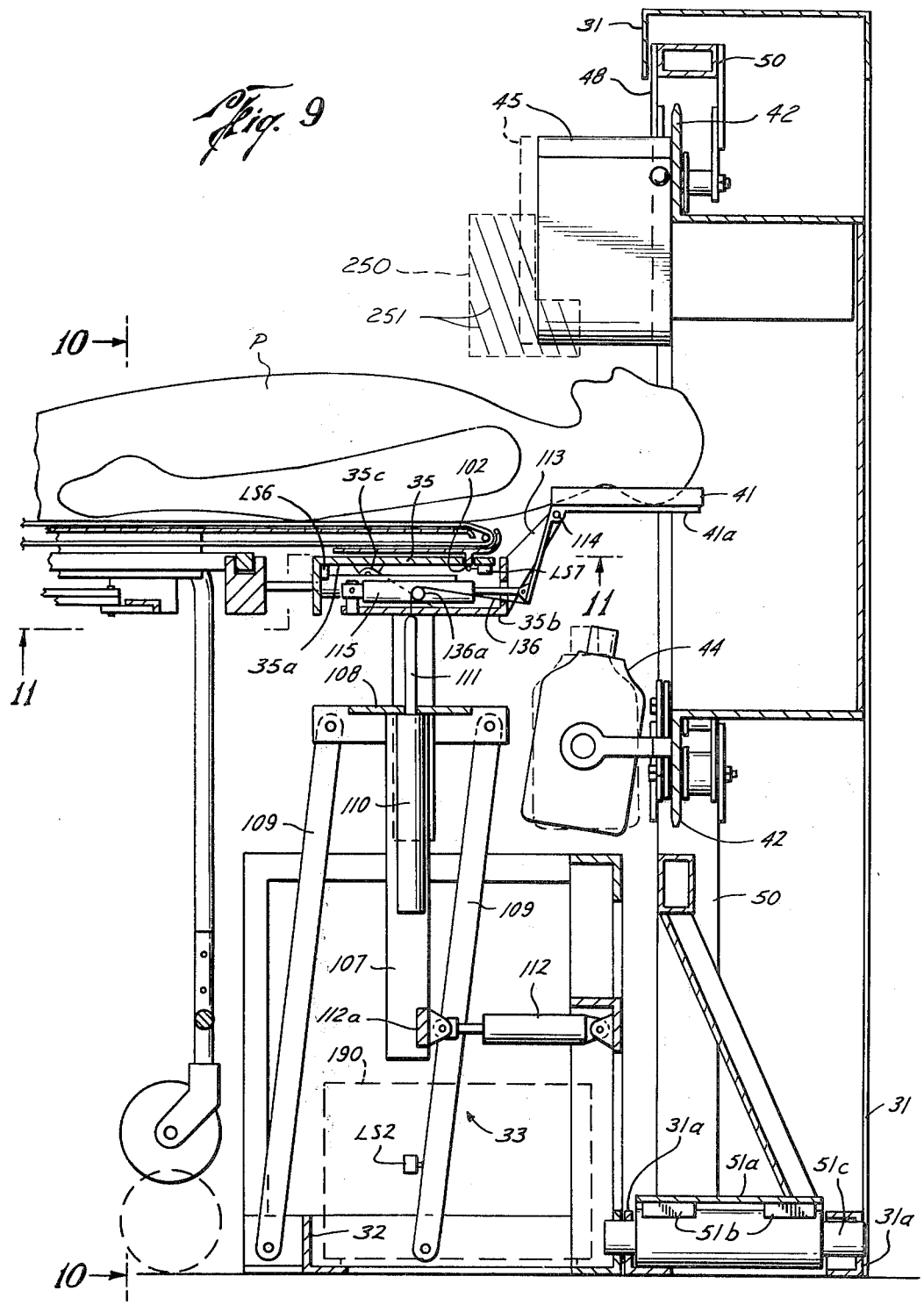

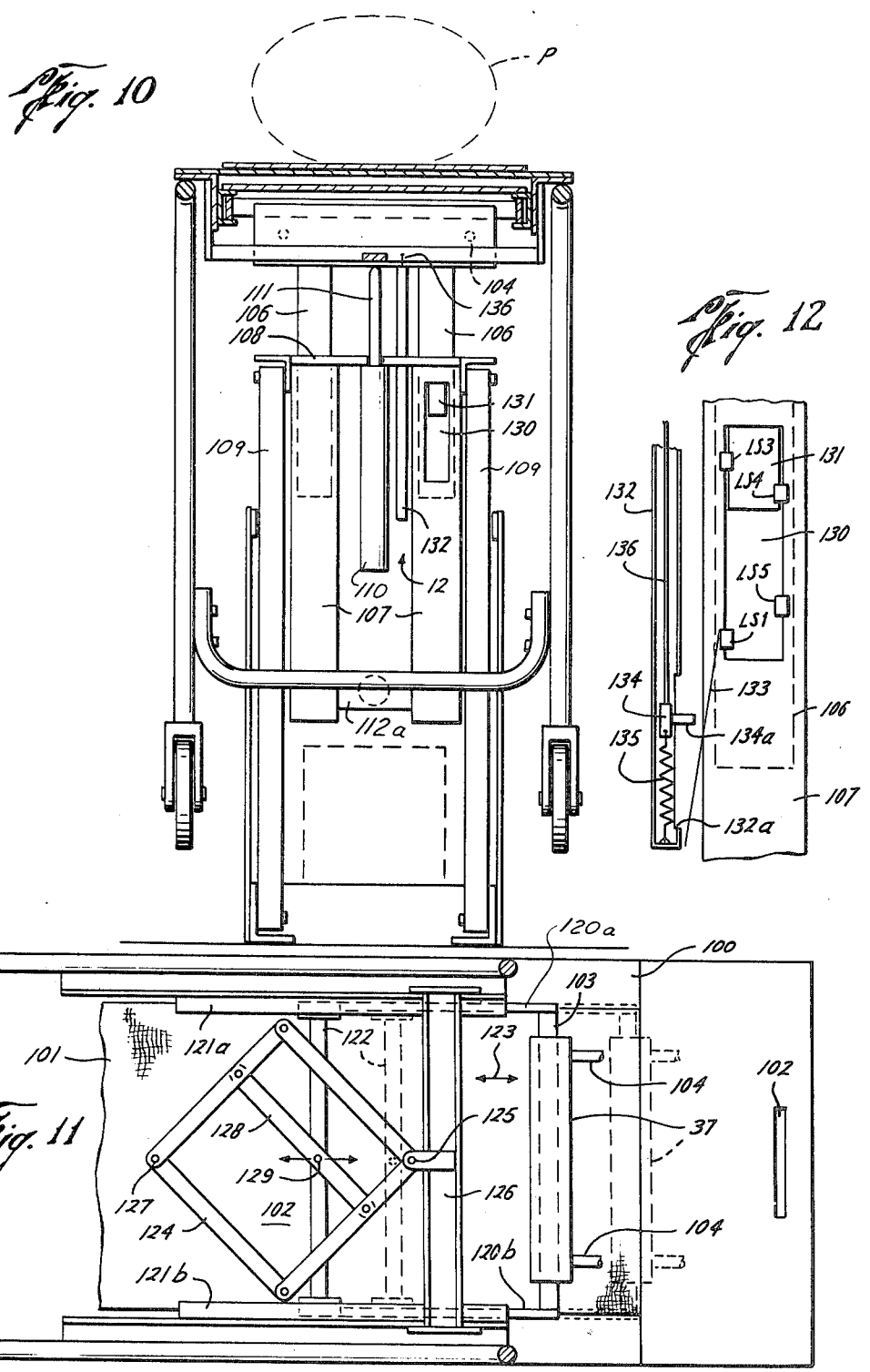

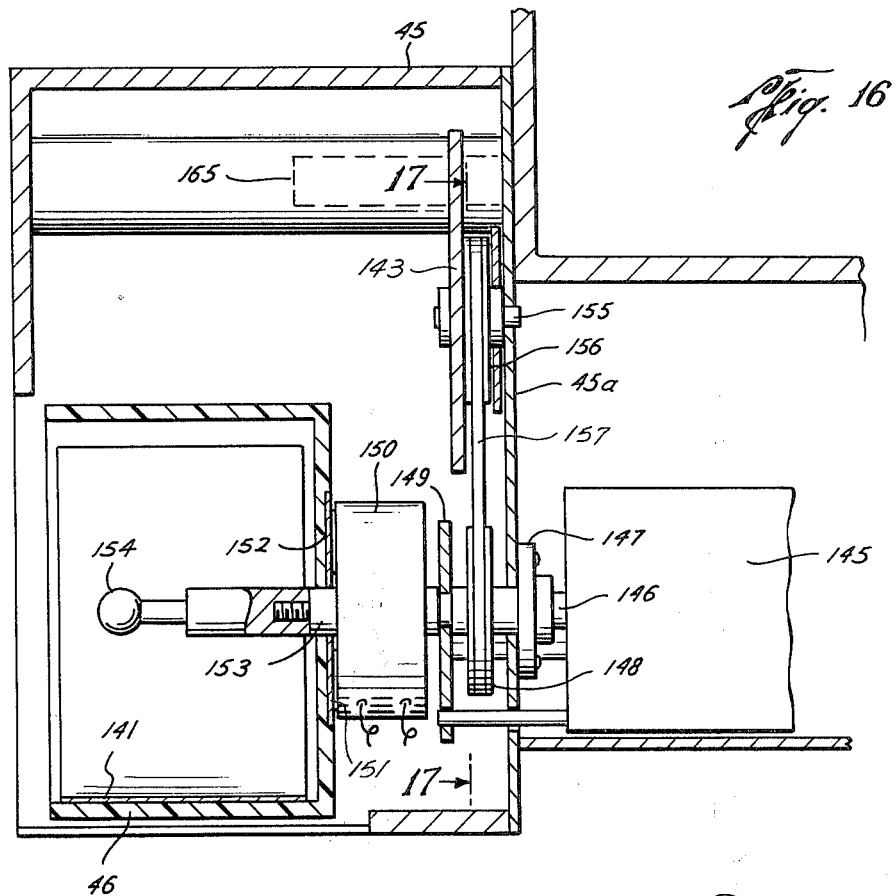
Fig. 16
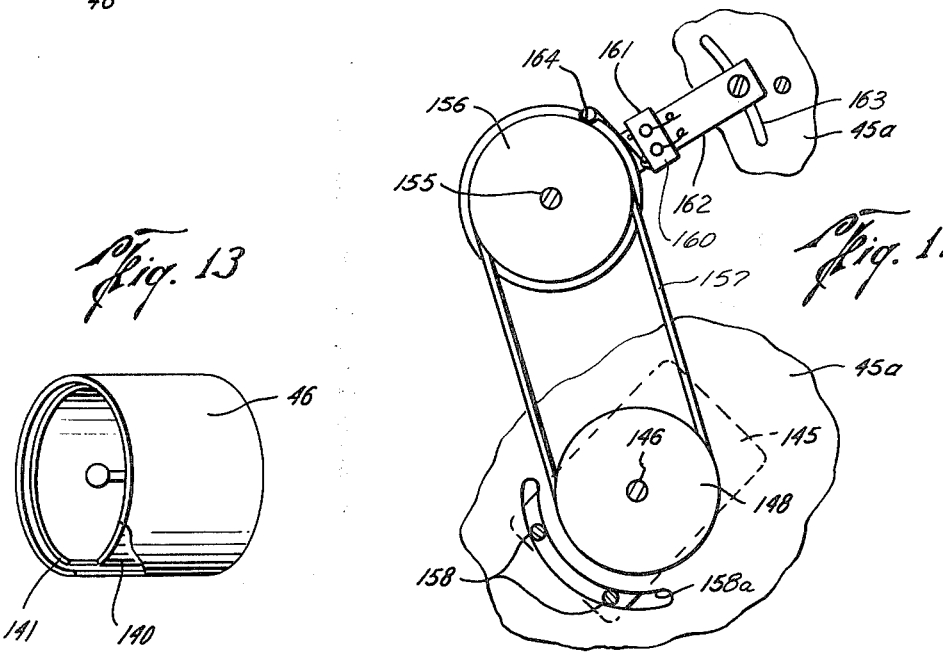
Fig. 13
Fig. 17

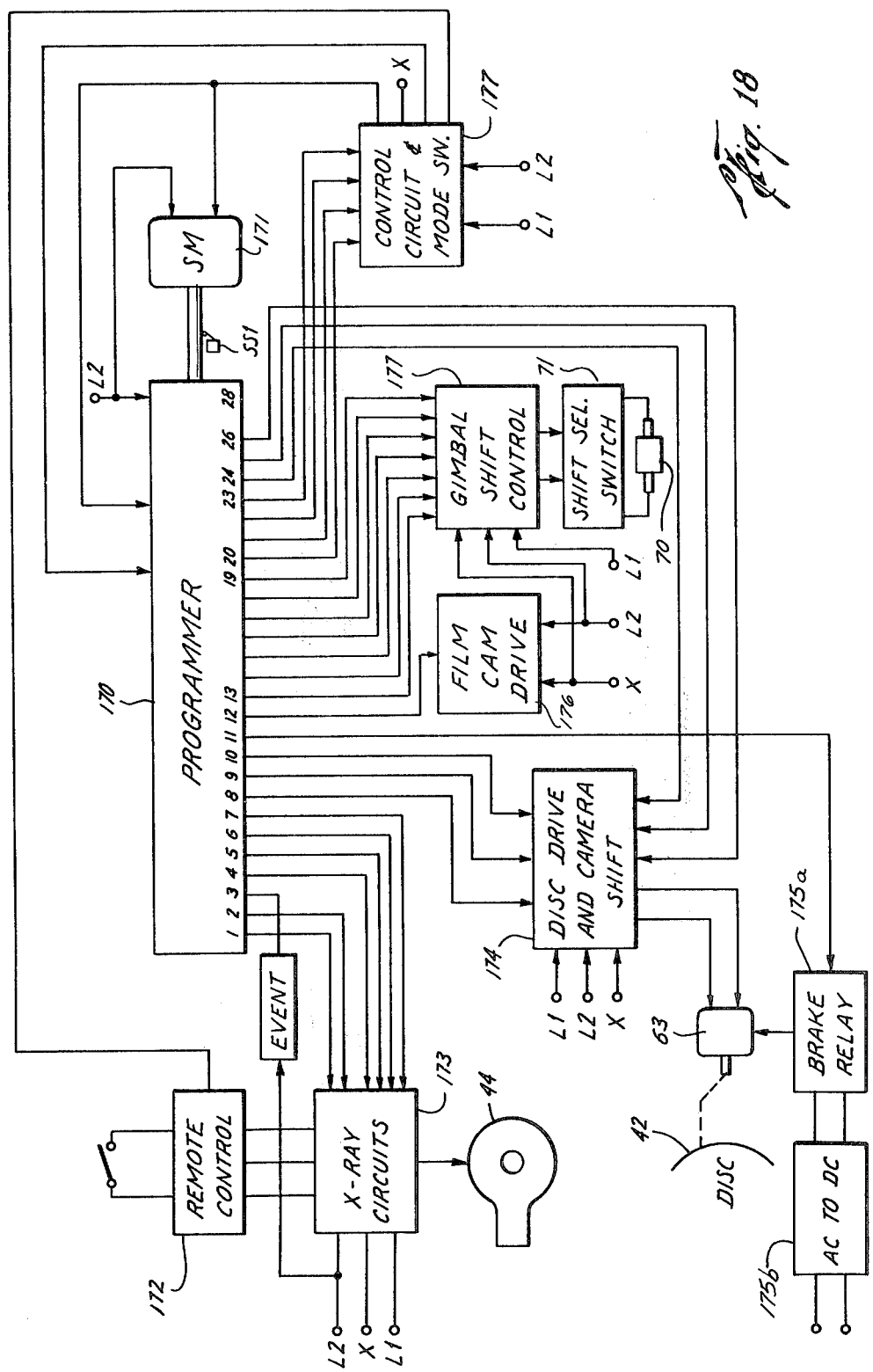

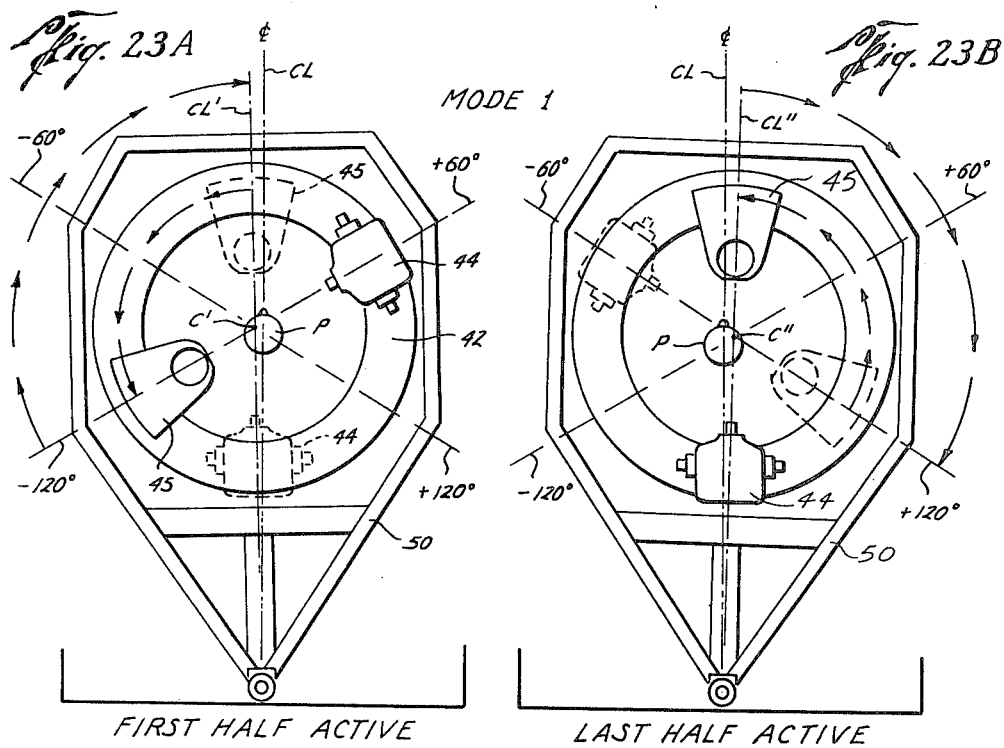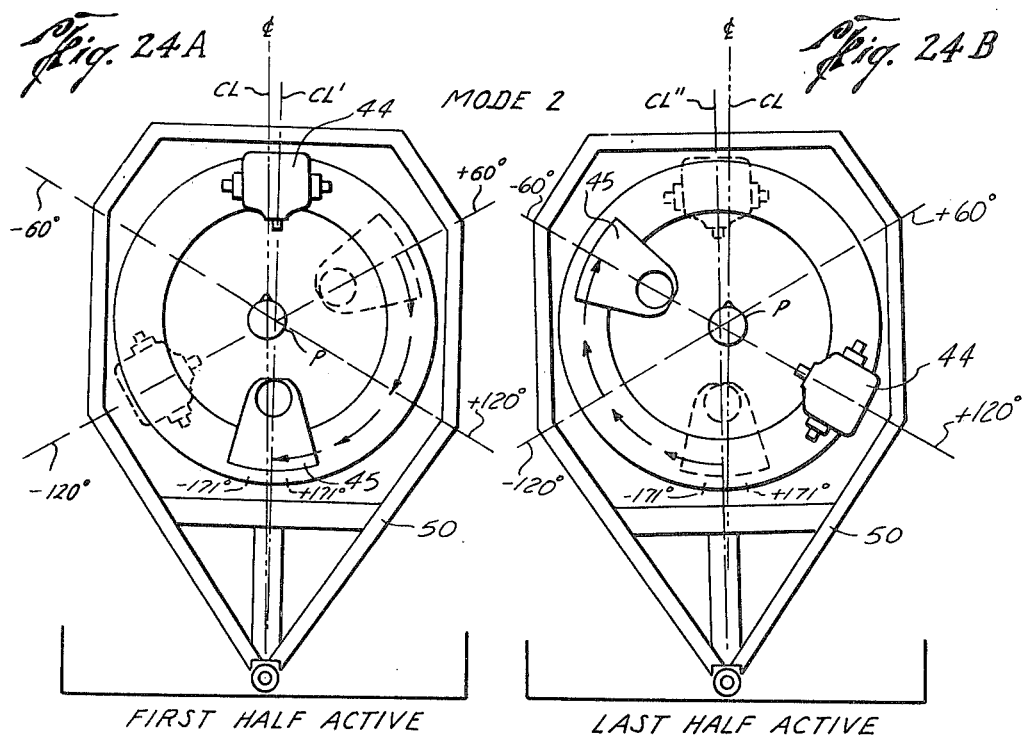

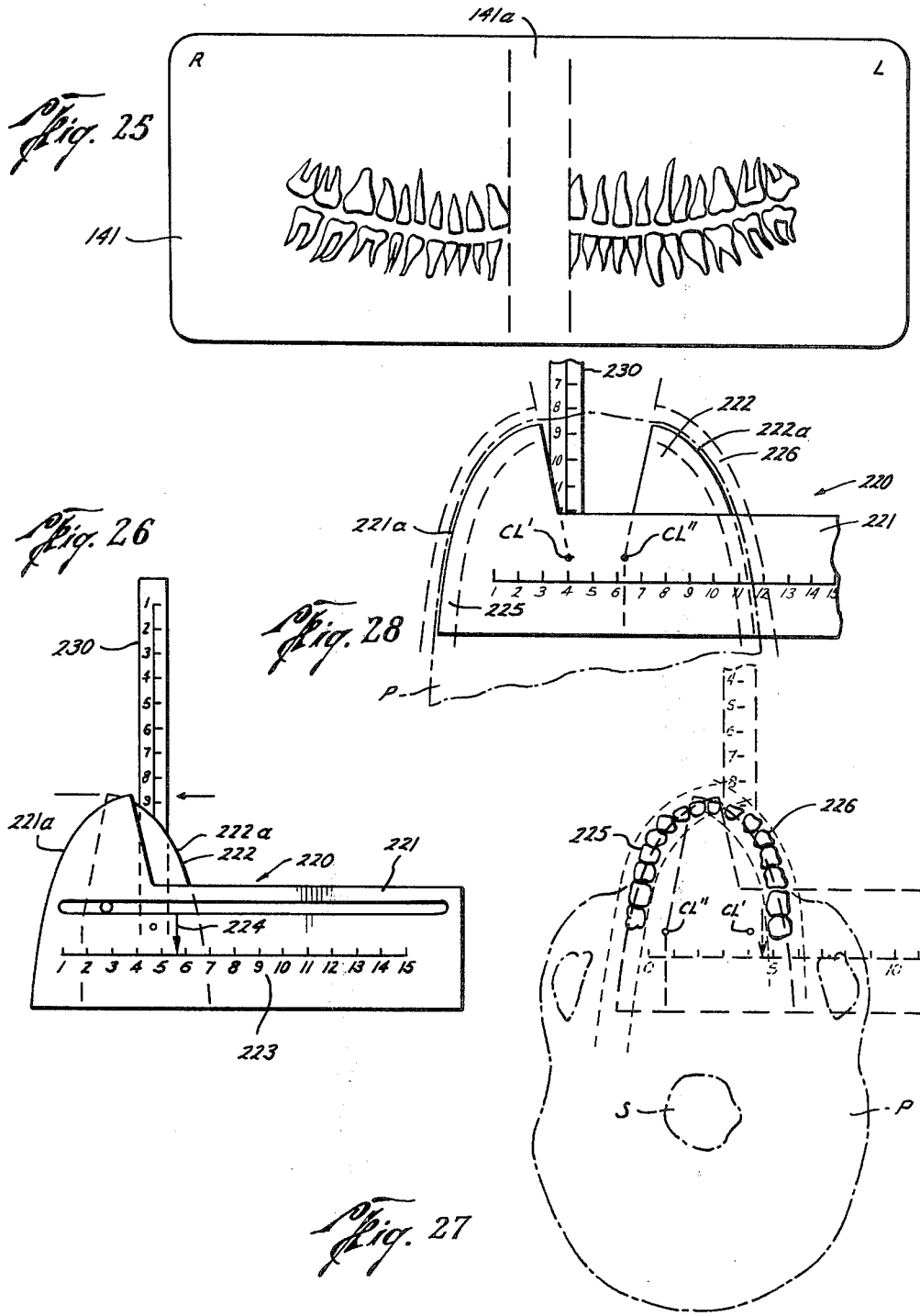

CONVEYER APPARATUS FOR MEDICAL PATIENTS

This is a division of application Ser. No. 429,482, filed Jan. 2, 1974 now U.S. Pat. No.. 3,908,126.

BACKGROUND AND SUMMARY OF THE INVENTION

This invention relates to apparatus and methods for providing selected, continuous radiographs of a subject, particularly of the human body, and in one of its aspects to such apparatus and methods which provide for such radiographs of a subject lying horizontal. The principles of this invention apply to the production of panoramic radiographs, tomographs, laminographs and zone laminographs of the human body. The specific apparatus and methods described herein are particularly adapted to providing for full mouth dental radiographs using a film lodated outside of the mouth, and providing radiographs of other portions of the human skull.

Throughout this specification, the particular radiographic apparatus described utilizes x-rays to provide radiographs and is referred to as an "x-ray apparatus" without any intent to limit its application to just rays in the x-ray spectrum.

Panoramic radiographs can be obtained by directing an x-ray beam through an object to be x-rayed to a moving x-ray film, while rotating the source and film about the object. In obtaining panoramic radiographs of a human subject, for example of the dental arch or selected portions of the skull, compensation must be provided for the fact that the curvature of the desired area of focus is generally not a true circle. In U.S. Pat. No. 2,798,958, apparatus is shown for obtaining radiographic projections of parts located internally of the human body, particularly full mouth dental radiographs using a single film outside the mouth. In the apparatus illustrated in that patent, the subject sits upright in a fixed position and an x-ray source and a single, extra oral, x-ray film are rotated about him. A cam mechanism is provided for varying the rate of film travel relative to the rate of travel of the x-ray source about the subject in order that the radiological projections occupy a distance on the film equal to the linear distance of a curved structure being x-rayed. To provide this, a plane-surfaced cam having a configuration corresponding to the curvature of the object to be visualized, such as the dental arch, has its center of rotation coincident with the center of rotation of a movable arm which supports the x-ray source and the x-ray film. The rotation of the cam is coupled to drive the film by a cable linkage.

Variation of the rate of motion of the film by virtue of the cam in the film driving mechanism compensates for the fact that the portion of the skull being x-rayed, for example, a dental half-arch, is a complex curve and not a circle.

Also, during x-raying of certain portions of the head, particularly the dental arch, it is highly desirable to shift the center of rotation of the x-ray source and film so that each half-dental arch can be x-rayed without projecting x-rays through the spinal column of the patient. In U.S. Pat. No. 2,798,958, this is accomplished by manually moving the patient after the completion of one-half of an x-ray cycle, to relocate the center of the axis of rotation with respect to the head of the patient. In x-raying either half of the dental arch, the center of rotation is chosen so as to fall at the center of an imaginary circle whose circumference would pass through the crowns of the molar teeth of the side being x-rayed. The resulting radiograph is in two half-arch sections on a single film with an unexposed space in the center of approximately one inch wide. In U.S. Pat. No. 3,045,118, an improvement is provided in the apparatus described in U.S. Pat. No. 2,798,958, wherein after x-raying of one-half of a dental arch, the apparatus automatically shifts the patient so that the line of sight between the x-ray source of the film bypasses the patient's spinal column and permits x-raying of the other half of the dental arch.

While the x-ray apparatus of U.S. Pat. Nos. 2,798,958 and 3,045,118 have proven to be highly satisfactory, particularly for providing radiographs of the dental arch, they also have certain limitations. For example, there are many times when it is highly desirable to provide for radiographs of a patient lying in a horizontal position. This is particularly true where the patient finds difficulty in sitting upright such as when he is injured or is seriously ill. In the past, numerous devices have been suggested for providing such x-rays, including panoramic x-rays where an x-ray source and x-ray film are rotted about a portion of a patient being x-rayed to obtain radiographic projections of that portion. Examples of such apparatus is shown in U.S. Pat. Nos. 3,082,322; 3,484,604; 3,466,439; 3,432,657; 3,549,885; and 3,486,022. In some of the apparatus of those patents, it is required that the patient be rotated rather than the x-ray source and film. In U.S. Pat. No. 3,229,088, a complex apparatus is provided for rotating the head of a patient (only partially) for taking radiographs of the dental arch.

Insofar as is known to applicants, none of the structures illustrated in these patents for providing x-rays of a subject in a horizontal position have resulted in a practical and economical x-ray apparatus which provides panoramic radiographic projections of selected portions of a subject lying horizontal, without undue discomfort or danger to the patient, and without relatively high cost. It is thus an object of this invention to provide such an apparatus.

A further limitation in the prior art referenced is that where a shift of the center of rotation is provided, either by shifting the patient or the x-ray apparatus, to position the line of sight of the x-ray apparatus with respect to the subject being x-rayed, the shift is fixed and the size and radius of the focal through remains constant. However, by providing a variable shift within safe limits, and by being able to accurately adjust the position of the subject in the x-ray machine, the focal through can be changed in size and location so that, for example, successive radiographs or tomographs can be made at selected, progressively deeper depths in a portion of the skull being examined to give, in effect, a three dimensional picture of the examined area. However, in order to provide this capability, suitable apparatus must be provided for providing the required shift, when selected. Also, once the shift is made variable, some means must be provided to ensure that the proper shift can be quickly selected for a desired operating condition and that the x-ray apparatus will automatically and accurately provide the selected operation, even when operated by a person with relatively little training in radiology.

Thus, another object of this invention is to provide an x-ray apparatus which is a substantial improvement over the prior art x-ray apparatus referenced, and provides for a variable shift which may be readily selected for a desired x-ray operation to greatly increase the range of practical usage of the x-ray apparatus. Further, presently available x-ray apparatus used in tomography generally costs several hundred thousands of dollars or more, thus limiting their availability and usage, and another object of this invention is to provide an x-ray apparatus which meets the previously stated objects, but which can produce tomographs and laminographs at a relatively lower cost for more general usage in medical and dental radiographic diagnosis. It is believed that the general availability of such an x-ray apparatus will greatly aid a large number of physicians and dentists in many of their diagnostic procedures.

Another object of this invention is to provide such an x-ray apparatus in which the center of rotation of the x-ray source and film can be shifted a variable amount without shifting the patient.

In the apparatus of U.S. Pat. No. 2,798,958, the x-ray film is loaded into a flat cassette having a center slit in the line of sight of the x-ray beam. The rotation of the cam mechanism utilized, which is mechanically driven by the motor causing the x-ray source and film holder to rotate, must be converted to a linear motion by a cable linkage connected to the rotating cam to move the x-ray film past the slit in the cassette. Unless the cable linkage is properly adjusted, it can introduce jitter into the movement of the x-ray film and distort the resulting radiograph. Also, the requirement for driving the cam directly from the motor rotating the x-ray source and film holder complicates the construction of the x-ray apparatus, and adds a further source of problems. Thus, another object of this invention is to provide a drive mechanism for moving the x-ray film during rotation of the x-ray source and film about an object being x-rayed without the need for a cable linkage, or for a direct connection to the x-ray excursion drive motor, while providing little or no jitter or other movement which would distort the resulting radiograph.

Another object of this invention is to provide such a drive mechanism which automatically adjusts the speed of movement of the film to compensate for variations in the curvature of the object being x-rayed.

A further object of this invention is to provide such a drive mechanism and film holder in which the x-ray film may be easily and rapidly loaded, orientated, and removed.

Another object of this invention is to provide such a drive mechanism in which the relative speed of rotation of the x-ray source and film holder, and the rate of movement of the x-ray film can be altered to permit panoramic radiographic projections to be taken of objects of different shapes while maintaining a substantially constant focus of the image. Because the apparatus of this invention readily provides for a selected variance in the amount of shift of the center of rotation of the x-ray source and film, and a selected variance in the shape of the focal trough during operation within preset limits, it can be used, for example, for providing successive tomographs of an area of examination so that each tomograph has a sufficient depth of focus to overlap with the next tomography and effectively provide a continuous, three dimensional picture of the examined area.

In the operation of any x-ray apparatus of the type contemplated by the present invention, particularly where relatively small selected areas are being examined, it is highly desirable that as little operator intervention as possible be required, and that the operator be required to make as few initial adjustments or settings as possible, to lessen the chance of operator error or misjudgement.

Thus, a further object of this invention is to provide automatic control apparatus for controlling the sequence of operation of an x-ray apparatus of the type provided by this invention, permitting selection by the operator of desired modes of operation and desired degrees of shift of the center or rotation of the x-ray source, which the apparatus will then automatically provide.

A further object of this invention is to provide improved patient conveying and elevating apparatus for rapidly and safely moving a patient who may be ill or injured into proper position in an x-ray apparatus with little or no physical handling of the patient during this procedure. Furthermore, another object of the present invention is to provide safety features which automatically prevent interference between the patient and the x-ray apparatus while the patient is being moved in and out of the machine, or while the x-ray apparatus is being operated. By use of the positioning apparatus of this invention, the patient can be safely and relatively precisely positioned in the x-ray apparatus within adjustable limits and this feature further adds to the flexibility of the present apparatus.

A further object of this invention is to provide a single x-ray apparatus which satisfies all of the above stated objects regarding radiographic capability, cost and availability, patient safety, and operator convenience.

These and other objects of this invention, which will be apparent upon consideration of the following detailed description of the drawings and of the appended claims and drawings, are accomplished in accordance with this invention by providing an x-ray apparatus for taking panoramic radiograph projections wherein an x-ray source and x-ray film holder are mounted in an upright frame to rotate in a vertical plane with respect to the frame, and about an object being x-rayed, while the film is moved past a lens or slit, and the center of rotation of the x-ray source and film holder can be shifted a selected amount by causing the frame to move with respect to the object being x-rayed. In the preferred embodiment of this invention illustrated, the upright frame is a pivoted gimbal frame mounted in turn on a fixed frame at a lower pivot point and means is provided for causing the frame to pivot about its lower pivot point a selected amount to shift the center of rotation of the x-ray source and film holder a selected amount. The x-ray source and film holder are preferably mounted on opposite sides of a centerless disc supported for rotation on the gimbal frame, and the disc is driven along its outer edge, which is beveled, by an electric motor through a novel arrangement of drive wheels so that the circumferential speed of the mating faces of the drive wheels and disc are equal at substantially the center of contact, and a smooth, precise movement of the disc is provided.

In the preferred embodiment illustrated, the means for causing a selected amount of shift includes a switch actuator for providing stepped increments of shift of the gimbal frame on either side of the vertical centerline of the frame. In this manner, the disc supporting the x-ray source and film holder for rotation can be rotated about one center of rotation when one-half of the x-ray scan is taken, and a second center of rotation when the other half x-ray scan is taken, so that, for example, a full dental arch can be x-rayed without projecting x-rays through the patient's spinal column.

Also, means is provided for controlling the rate of movement of the x-ray film passing the x-ray slit. In the preferred embodiment of this invention, the x-ray film is placed in a cylindrical cassette which is mounted for rotation in the film holder. A constant speed electric motor is provided for rotating the cassette at substantially the speed of rotation of the disc supporting the x-ray source and film holder, except that the speed of rotation of the cassette is varied as required to compensate for variations in the shape of the area being x-rayed. The housing of the film drive motor is mounted to float with respect to the film holder and a sloped cam mechanism is connected directly between the rotating shaft of the motor and the floating housing so that the differential speed of rotation of the shaft with respect to the housing is a function of the shape of the cam. The shape of the sloped cam for a particular x-ray operation can be determined by translating the change in radius of a basic cam as described herein which would provide the required change in the rate of movement of the film.

In accordance with this invention, a slide rule profile projector is provided to aid in determining the required shift for a particular x-ray operation. The profile projector includes curved faces corresponding to the best line of focus of the x-ray apparatus for a particular sloped cam. The curved faces are movable towards and away from each other and by overlaying the curved faces on an outline of the object to be x-rayed (each curved face representing one-half of the x-ray) and noting the spacing between the faces, the required amount of shift can be determined. An important feature of the preferred embodiment of this invention illustrated is that the stepped increments of gimbal shift can be numbered on a switch selector so that the same shift will be provided each time the same number is selected by the operator, and a scale of numbers can be provided on the profile projector corresponding to the shift selector numbers. Thus, if the shift reading on the profile projector for the best line of focus of a particular area to be x-rayed is, for example, 5, then the operator need only select shift position 5 on the shift selector of the x-ray apparatus and the required shift will be provided.

The preferred form of x-ray apparatus of this invention illustrated also includes a patient conveyor cart having a movable conveyor belt to aid in movement of the patient to and placement of the patient in the apparatus, and hydraulically operated patient elevator apparatus for properly positioning the patient in the apparatus. Safety limit switches are suitably located to automatically control the operation of the hydraulic elevator apparatus to avoid interference between the patient and the x-ray apparatus while the patient or the x-ray apparatus is being moved with respect to each other.

Other features of this invention are described in the following detailed description of the drawings.

DETAILED DESCRIPTION OF THE DRAWINGS

In the drawings, wherein like reference numerals are used throughout to designate like parts, and wherein preferred embodiments of the present invention are disclosed, FIG. 1 is a perspective view in elevation of the preferred form of x-ray apparatus of the present invention;

FIG. 3 is a view in elevation showing the switching mechanism for setting the shift of the center of rotation of the apparatus in FIG. 2;

FIG. 4 is a sectional view through 4—4 in FIG. 3;

FIG. 5 is a front elevation taken generally at 5 in FIG. 4;

FIG. 6 is a sectional view taken at 6—6 in FIG. 2;

FIG. 7 is a perspective view of the elevator pedestal of the apparatus of FIG. 1 and of a portion of a patient conveyor cart prior to connection with the pedestal;

FIG. 8 is a view taken at 8—8 in FIG. 7, except that the cart has been moved in position prior to elevation of the cart and the patient;

FIG. 9 is a sectional view similar to FIG. 8, extended through the line 9—9 in FIG. 2, and showing the patient in position in the apparatus of FIG. 1 with the pedestal and belt conveyor raised;

FIG. 10 is a view taken at 10—10 in FIG. 9;

FIG. 11 is a view taken at 11—11 in FIG. 9, showing the underside of the conveyor cart;

FIG. 12 is an enlarged view taken at 12 in FIG. 12;

FIG. 13 is an elevation view of a preferred form of cylindrical film cassette utilized with the present invention;

FIG. 16 is a view taken at 16—16 in FIG. 15;

FIG. 17 is a sectional view taken at 17—17 in FIG. 16;

FIG. 18 is an overall schematic of a preferred form of electrical control system, and programmer apparatus for the x-ray apparatus of FIG. 1;

FIGS. 23A and 23B show the positions of the apparatus of FIG. 2 during mode 1 operation;

FIGS. 24A and 24B show the positions of the apparatus of FIG. 2 during mode 2 operation;

FIG. 25 is a pictorial representation of a sample x-ray provided by the present apparatus in the dental mode;

FIG. 26 is a view in elevation of a slide rule type profile projector for use with the present invention;

FIG. 27 is a schematic view showing an imaginary outline of a section through a patient's head to illustrate the application of this invention in x-raying the dental arch; and FIG. 28 is a view similar to FIG. 27, except that a lower skull projection is taken to illustrate the application of the present invention in x-raying through the base of the skull.

GENERAL DESCRIPTION

Figure 1:
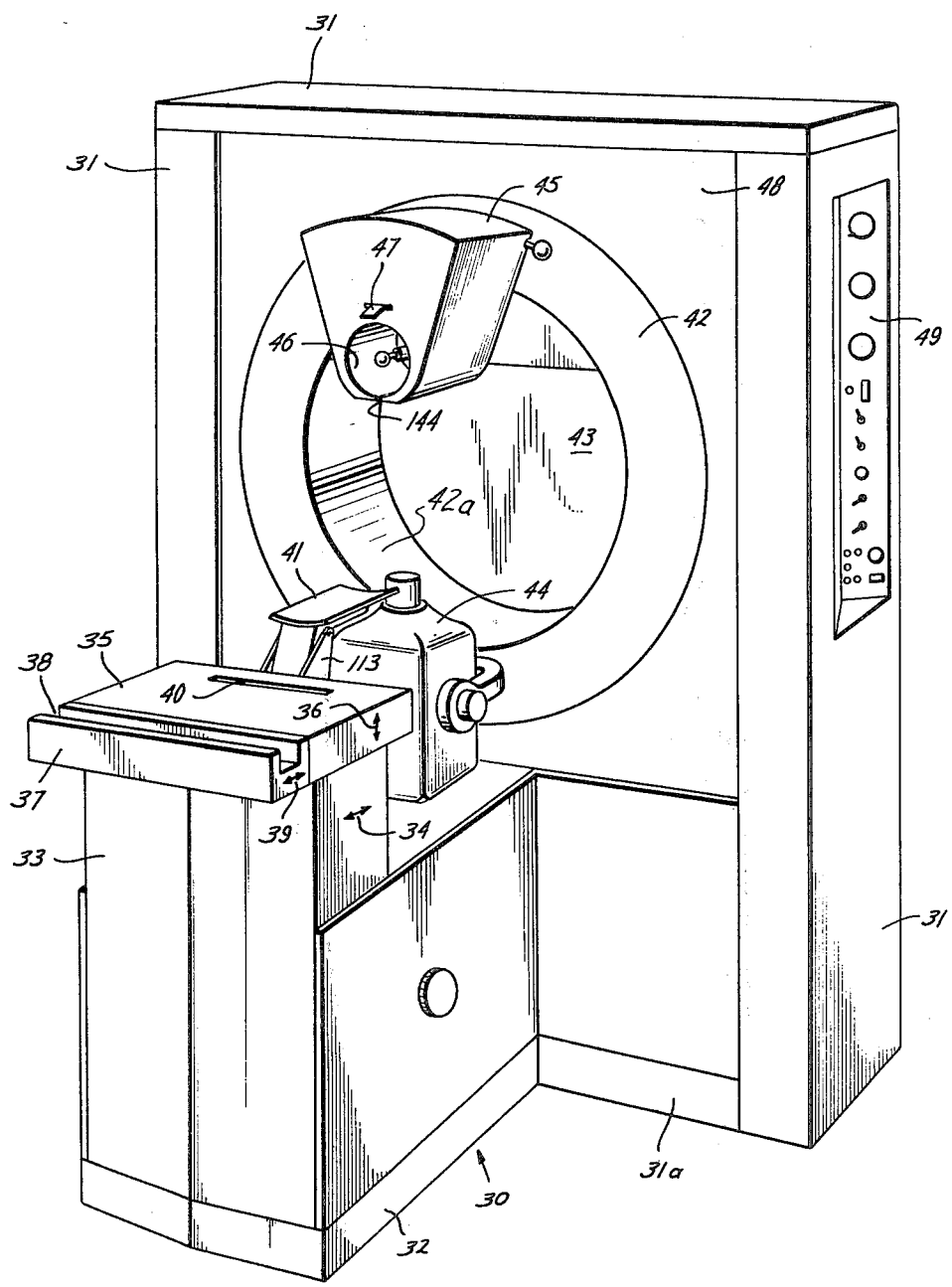

Referring now to the drawings, in FIG. 1, a preferred form of x-ray apparatus 30 of this invention is illustrated as including an upright frame and housing 31 and base frame 31a forming a box-like structure, and a box-like patient elevator pedestal 32 mounted in front of housing 31. Elevator pedestal 32 includes an elevator apparatus 33 movable in and out (i.e., towards and away from housing 31) as indicated by the arrow 34, and a patient support platform 35 mounted on elevator apparatus 33 for movement up and down as indicated by the arrow 36. As shown in FIG. 9, platform 35 is in the form of a hollow box and includes a top plate 35a pivotally mounted on a bottom plate 35b by brackets 35c mounted on each side of bottom plate 35b (only one bracket 35c is shown in FIG. 8). A slotted block 37 is mounted on platform 35, and includes an elongated slot 38 therein for controlling the movement of a belt on a patient conveyor cart as illustrated in FIGS. 7–12. Block 37 is movable towards and away from housing 31 as indicated by arrow 39. Platform 35 also includes an elongated slot 40 for interconnection with a bar on the front of a patient conveyor cart as hereinafter described. Extending from platform 35 and towards housing 31 is a patient headrest 41 which is also movable to adjust the tilt of the patient's head as hereinafter described. The apparatus for raising and lowering the respective members of pedestal 32 described is illustrated in FIGS. 7–12 and will hereinafter be described in detail. Elevating apparatus 33 on pedestal 32 functions to support the patient at the proper elevation and in the proper position within the x-ray apparatus for the x-raying operation.

A rotatable disc 42, defining a generally circular opening 43, is mounted in x-ray apparatus 30 as hereinafter described. A cylindrical member 42a extends from the edge of disc 42 defining opening 43 into apparatus 30. As illustrated in FIG. 1, an x-ray source 44 and an x-ray film holder or housing 45 including a cylindrical film cassette 46 are mounted on the opposite sides of disc 42 adjacent opening 43 so that they face each other, and are spaced apart a sufficient distance to permit the head of a patient to be inserted between them. The mounting and operation of disc 42 and source 44 are shown in FIGS. 2, 6, 23A, 23B, 24A and 24B, and the configuration and operation of the film holder 45 is illustrated in FIGS. 13–17. A retractable tape measure 47 may be mounted on the inside of housing 45 for measuring the correct patient head to film distance during operation of apparatus 30.

Figure 2:
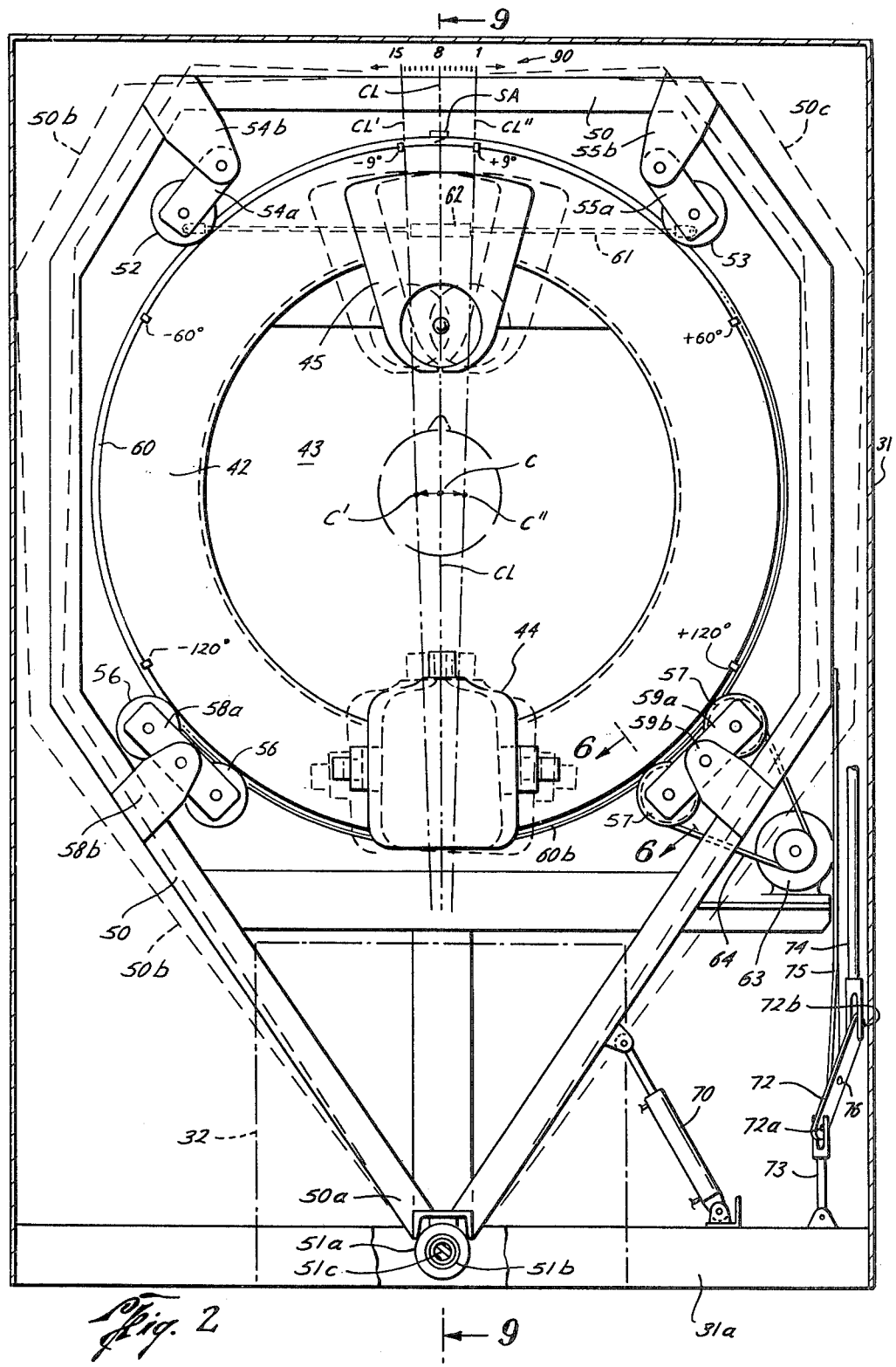
FIG. 2 is a frontal view in elevation of the apparatus of FIG. 1 with the elevator pedestal and front panel removed.
Figure 14A:
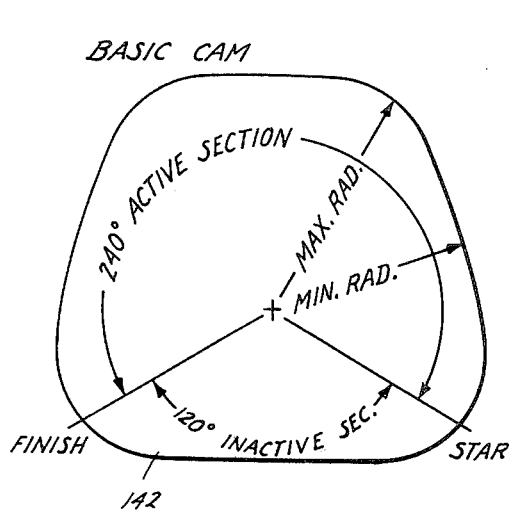
FIG. 14A is a schematic view of a basic cam defining the desired rate of movement of the x-ray film during an x-ray scan.
Figure 14B:
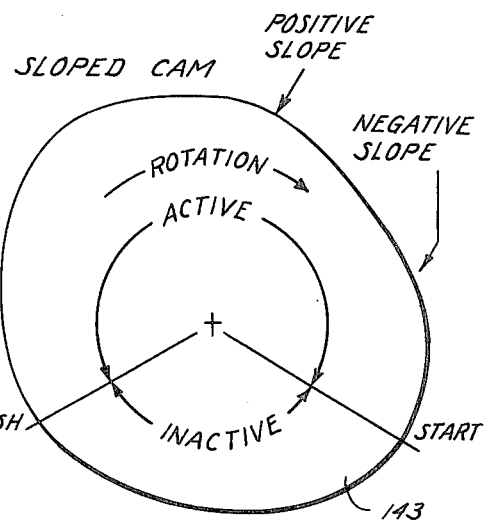
FIG. 14B is a schematic view of a modified cam of the present invention defining this rate of movement.

Disc 42 is mounted to rotate in an opening in a front plate 48 which is, in turn, mounted on a suitable frame which is illustrated in detail in FIG. 2. During operation, the head of a patient to be x-rayed is supported on headrest 41 between x-ray source 44 and film housing 45 so that as disc 42 rotates, it carries x-ray source 44 and film housing 45 about the head of a patient in a manner similar to the apparatus in U.S. Pat. Nos. 2,798,953 and 3,045,118, except that the patient is upright in those patents instead of horizontal. Also, while the shift required to provide a panoramic x-ray through certain areas to be x-rayed in those patents is provided by shifting the position of the patient with respect to the center of rotation of the x-ray source and film, this shift, when required, is provided in the present invention by shifting the center of rotation of disc 42, and providing for variations in the degree of this shift.

Suitable control apparatus 49 for providing the required electrical switching and control functions to operate the elements described of x-ray apparatus 30 is shown as being mounted in the upper righthand portion of housing 31, as, for example a removable sub-panel. Details of this apparatus are illustrated in FIGS. 3–5 and 18–22.

Of course, an x-ray apparatus constructed in accordance with the principles of this invention may take many different forms, other than the general arrangement described with respect to apparatus 30.

GIMBAL SHIFT AND DISC DRIVE APPARATUS

As noted, an important feature of the present invention is the provision for shifting the center of rotation of disc 42 during operation rather than shifting the patient.

Referring now to FIG. 2, preferred apparatus for providing this shift is shown as including a pivoted gimbal or operating frame 50 mounted inside housing 31 for supporting disc 42 for rotation. As illustrated, frame 50, which may be made of lightweight aluminum tubing, has its lower end 50a in the form of an apex of a triangle and this end is provided by a tubular sleeve 51a mounted by spaced bearings 51b (see FIG. 9) to pivot on a rigid pivot pin 51c which is, in turn, mounted in base frame 31a of apparatus 30. By this arrangement, frame 50 can pivot about pin 51c to shift between the dotted line positions 50b and 50c inside of housing 31, which are on either side of the center shift position illustrated by the solid line position of frame 50 in FIG. 2. As illustrated in FIG. 2, single, V-grooved rollers 52 and 53 are rotatably mounted on the upper portion of the frame 50 and on opposite sides thereof by arms 54a and 55a, respectively, and each of arms 54a and 55a are respectively pivotally supported on frame 50 by brackets 54b and 55b. Also, opposed pairs of V-grooved rollers 56 and 57 are rotatably mounted on opposite sides of frame 50, below rollers 52 and 53, on opposed plates 58a and 59a, respectively, and plates 58a and 59a are in turn respectively pivotally mounted on brackets 58b and 59b connected to gimbal frame 50. Rotatable disc 42, which may be made of a piece of flat aluminum with opening 43 in the center, includes a beveled outer edge 60 having converging beveled surfaces 60a and 60b, and disc 42 is mounted between and supported on rollers 52, 53, 56 and 57 with edge 60 supported in the grooves of the rollers as shown in FIG. 6. An adjustable rod 61, which may be adjusted in length by a turnbuckle 62, may be connected between arms 54a and 55a to adjust the force with which rollers 52 and 53 engage beveled edge 60 of disc 42. A pulley 65 may be rigidly connected to each of rollers 57, and mounted to rotate with the roller, and pulleys 65 may be driven by a constant speed motor 63 through an endless belt 64 connected to pulleys 65 (see FIG. 6). Of course, if desired, rollers 56 can be driven instead of rollers 57. As illustrated in FIG. 6, the V-groove of each of rollers 57 includes converging surfaces 57a and 57b, so that these surfaces are engaged with a corresponding surface of edge 60 of disc 42 to provide a ripple free, precision drive which is highly responsive and capable of withstanding continuous directional changes during rotation of the disc and the structures mounted on it. To accomplish this, the relationship between V-groove surfaces 57a and 57b of rollers 57 and beveled edge 60 of disc 42 is such that the circumferential speed of the mating members agrees at a center line 66 representing the true pitch diameter of the disc. On either side of line 66, the circumferential speed of the mating members is in conflict, but of opposing character so that the direction of their components of motion cancel each other. Thus, in the area represented by the arrows 69, the circumferential speed of disc 42 exceeds that of rollers 57, and in the area represented by the arrow 68 the opposite is true. As a result, although disc 42 supports a relatively heavy stationary load, driving rollers 57 are not subject to compression so that relatively small rollers, which can be made of phenolic or similar material, can effectively and efficiently rotate a relatively large disc carrying a relatively heavy weight, for example, in the order of 120 pounds, at a constant speed of, for example, 2 rpm.

Figure 19:
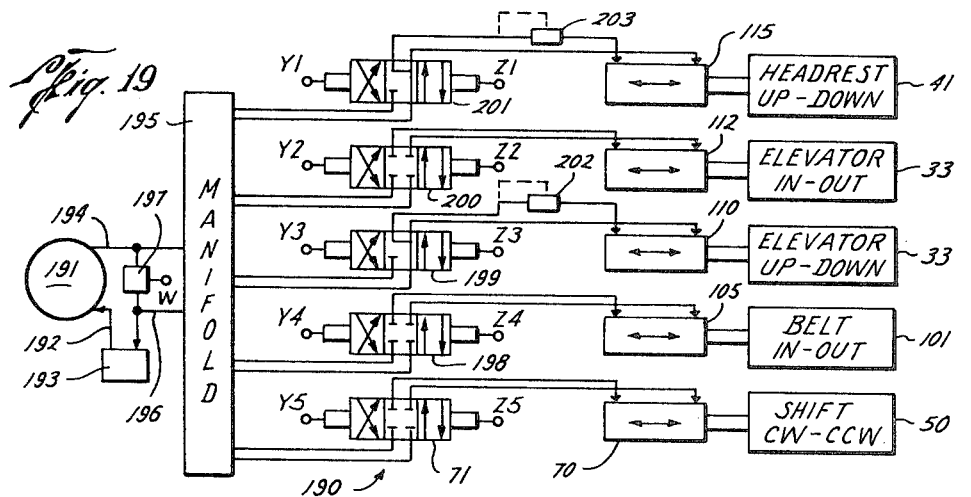
FIG. 19 is a schematic view of a preferred form of a hydraulic system for the x-ray apparatus of FIG. 1.

Referring again to FIG. 2, the preferred apparatus illustrated for shifting the position of gimbal frame 50 within housing 31 includes a double acting hydraulic cylinder 70, which is controlled by a four-way, three-position solenoid valve 71, illustrated in detail in FIG. 19. A shift control means is preferably mounted in the lower portion of housing 31 for responding to the shift in position of frame 50 to control the extent of the shift. A preferred form of this means is illustrated as including a lever arm 72 pivotally mounted at one end 72a to a linkage rod 73, and pivotally mounted at its other end 72b to an upwardly extending rod 74. Linkage rod 73 is also pivotally mounted at its lower end to the base frame 31a of housing 31. At a point 76, intermediate its ends, arm 72 is pivotally connected to an actuator rod 75 which is connected to frame 50 so that the motion of frame 50 between its respective shift positions is identically tracked at intermediate pivot point 76. Intermediate pivot point 76 is located so that the distance between the end pivot points 72a and 72b of lever arm 72 is four times the distance between pivot point 76 and the end pivot point connected to linkage 73, so that the motion of rod 74 in a vertical direction is four times the motion of arm 75 in response to the shift of frame 50. As shown in FIGS. 3 and 4, rod 74 is connected at its upper end, in the upper portion of housing 31, to operate a shift selector mechanism generally designated by the numeral 77. A preferred form of such a selector mechanism is illustrated as including a switch actuator 78 which is mounted in an elongated slot 78a in the center of a plate 79, and switch actuator 78 is connected to the upper end of rod 74 to follow the movement thereof. Elongated slots 80 and 81 are also located in plate 79 on either side of slot 78a and function as guides for microswitches 82 and 83, respectively, which are mounted to be actuated by actuator 78 and to move back and forth in the slots to different positions representing different desired shifts of gimbal frame 50, with switch 82 representing the left limit of shift and switch 83 representing the right limit of shift. A third microswitch 78b is mounted to be actuated by actuator 78 on the back of plate 79, adjacent the center of slot 78a, and switch 78b represents the center position of shift of frame 50. As illustrated in FIG. 3, an endless cable 84 is connected between spaced pulleys 85 and 86 mounted, respectively, on the upper and lower ends of plate 79, and each of switches 82 and 83 is rigidly connected to cable 84 to move in its respective guide slot under control of cable 84. Pulley 85 is mounted on a shaft 87 which is, in turn, connected to operate a rotary switch 88, and shaft 87 extends through housing 31 to be actuated by a pointer knob 89 as illustrated in FIGS. 4 and 5. By adjusting the rotary position of shaft 87 by knob 89, switches 82 and 83 can be moved from a position representing the maximum shift of frame 50 in one direction, wherein switch 82 is adjacent to the upper end of slot 80 and switch 83 is adjacent the lower end of slot 81, to a central position in which switches 82 and 83 are located in their respective slots directly across from each other, and to a position representing the maximum shift of frame 50 in the opposite direction, wherein switch 82 is located adjacent the lower end of slot 80 and switch 83 is located adjacent the upper end of slot 81.

Of course, switches 82 and 83 may be set at positions between the described extreme positions, and center position. As indicated in FIG. 5, the extreme positions of switches 82 and 83 may be represented by positions 1 and 15 indicated for pointer knob 89, the center position by knob position 8, with intermediate positions represented by knob positions 2–7 and 9–14. Referring to the area marked generally by the numeral 90 in the top of FIG. 2, maximum shift positions of the axis of rotation of disc 42 are indicated, along with intermediate positions corresponding to the numbers 1–15 as in FIG. 5. In the illustration given, numeral 8, which would represent a position wherein switches 82 and 83 are located near the center of slot 80 and 81 and are across from each other, represents zero or no shift. Thus, during operation of the apparatus of FIG. 2, knob 89 can be set to provide a desired degree of shift within the limits described. Also, pulleys 85 and 86 can be sized so that each of positions 1–15 is a 20° step of shaft 87 and causes a one centimeter movement of each of switches 82 and 83, which in turn causes a one-half centimeter shift of the center of rotation of disc 42. Thus, the amount of shift of frame 50 can be accurately controlled.

Figure 20:
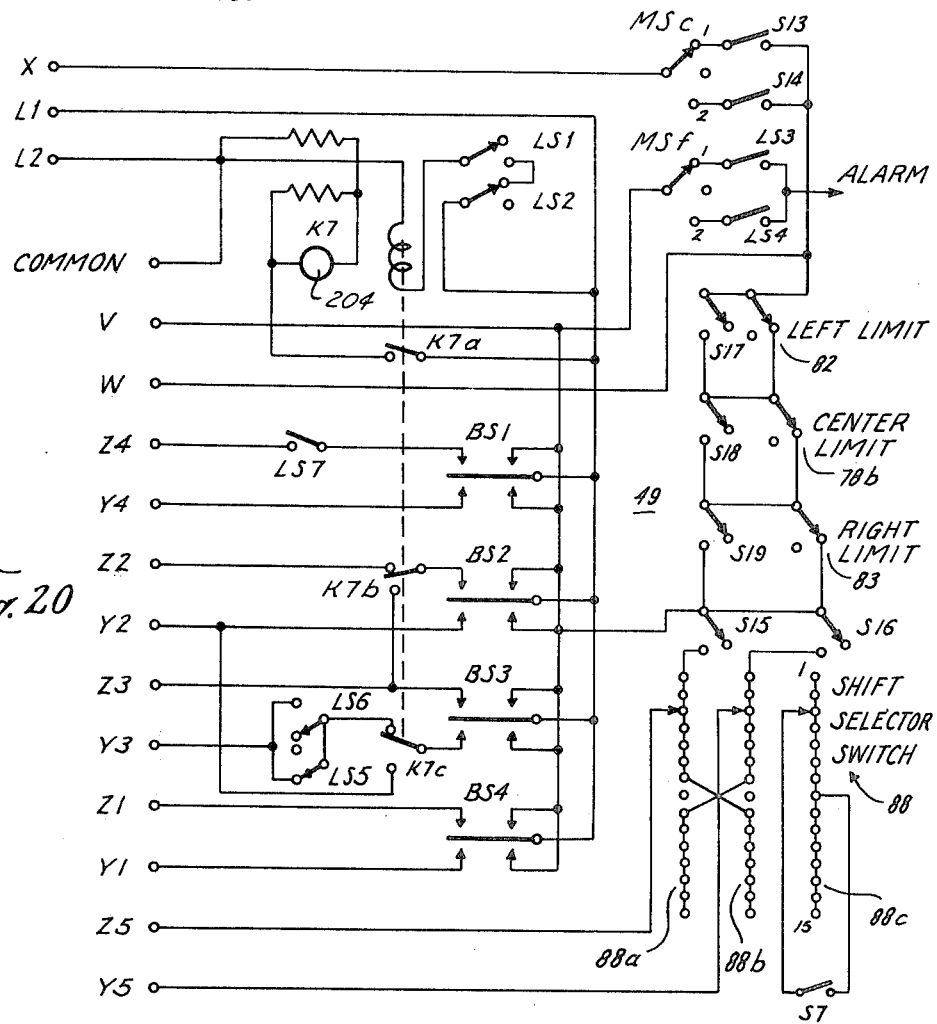
FIG. 20 is an electrical schematic of the switching apparatus for the hydraulic system of 19, and for the shift selector switch mechanism of FIG. 3.

The electrical schematic of switch 88 is shown in FIG. 20, and the hydraulic schematic of the valve 71 for controlling shift cylinder 70 is shown in FIG. 19.

PATIENT CONVEYOR AND ELEVATOR MECHANISM

Referring now to FIGS. 7–12, a patient conveyor cart 100, supported on wheels for portability, is illustrated as including a patient P lying on a belt conveyor 101 on top of the cart. In FIG. 7, elevator apparatus 33 is shown extended away from x-ray apparatus 30 and in its lower position for receipt of cart 100. Cart 100 also includes a guide bar 102 located underneath the front end of the cart, and the cart also includes a second bar 103 spaced towards the rear of the cart from bar 102, which, as described in FIG. 11, operates a mechanism for moving belt conveyor 101 to shift the patient from a position shown in FIGS. 7 and 8 to a position such as shown in FIG. 9.

As shown in FIGS. 8 and 9, patient elevator apparatus 33 includes apparatus for moving belt conveyor 101 in and out to move the patient from a position on cart 100, to the position wherein his head is lying on headrest 41; apparatus for moving cart 100 and the patient to the correct elevation for movement of the patient into machine 30; apparatus for moving patient P and cart 100 inwardly and outwardly from machine 36 when the patient is at the proper elevation; and apparatus for tilting headrest 41 for proper positioning of the patient's head.

As illustrated in FIG. 8, the apparatus for moving belt conveyor 101 includes block 37 which is connected through piston rods 104 (only one shown) to spaced hydraulic cylinders 105 mounted inside of platform 35. As shown in FIG. 8, conveyor 100 is lifted to insert bar 102 in slot 40 of platform 35 and bar 103 in slot 38 of movable block 37, with cylinders 105 retracted as shown in FIG. 7.

As shown in FIG. 10, platform 35 is supported by parallel arms 106 which telescope into tubular members 107 mounted on a generally rectangular platform 108 which is, in turn, pivotally mounted at their lower ends to the lower frame of pedestal 32 so that arms 109 supporting platform 35 form a parallelogram movable between the positions shown in FIGS. 8 and 9. A hydraulic cylinder 110 is vertically mounted on platform 108 in the approximate center thereof, and includes a piston rod 111 standing upwardly and secured to lower plate 35b of platform 35 for moving it up and down between the lower position shown in FIG. 8 to the upper position shown in FIG. 9. Thus, when patient conveyor cart 100 has been supported on extendable block 37 and platform 35, as shown in FIG. 8, cylinder 110 can be actuated to raise the platform 35 to a position in which a patient can be moved inwardly towards machine 30, and this operation will raise cart 100 off the ground so that it is no longer supported by its front wheels.

The apparatus for moving elevator mechanism 33, and thus patient P, towards and away from machine 30 includes a hydraulic cylinder 112 mounted inside of pedestal 32 and connected to a cross member 112a connected between the lower end of tubular members 107. As shown in FIG. 8 when cylinder 112 is extended, apparatus 33 is in its outward position and when cylinder 112 is retracted, as shown in FIG. 9, apparatus 33 is in its inward position wherein the patient is located with his head between x-ray source 44 and film housing 45.

Headrest 41 is mounted on an angled plate 41a which is pivotally supported by parallel plates 113 on the back wall of platform 35 (see FIG. 1). Plate 41a is pivotally connected at a pivot point 114 to parallel plates 113 and extends from pivot point 114 to the piston rod of a hydraulic cylinder 115 mounted inside of platform 35, so that as piston rod is extended or retracted, headrest 41 pivots to provide different positions of tilt for a patient's head.

As previously noted, top plate 35a of platform 35 and block 37 is pivotally mounted with respect to bottom plate 35b to follow the horizontal level of cart 100 when elevated off of its front wheels.

The electrical control and hydraulic control apparatus for controlling the operation of hydraulic cylinders 105, 110, 112 and 115 are illustrated in FIGS. 19 and 20 and their operation is hereafter described in detail.

Referring now to FIG. 11, a preferred form of a patient conveyor mechanism for cart 100 is illustrated for driving belt conveyor 101 which may be an endless belt made of a flexible material preferably with a low coefficient of friction mounted for rotation about rollers (not shown) on the opposite ends of cart 100. The conveyor mechanism includes a slide mechanism 120 having bar 103 at one end connected to parallel spaced apart rods 120a and 120b, which are in turn slidably mounted inside slotted, parallel guides 121a and 121b mounted on each side of conveyor belt 101 and adjacent its longitudinal edges. The other ends of rods 120a and 120b are connected to a cross member 122, parallel with and spaced from bar 103, so that as bar 102 is moved in the direction of arrow 123, cross member 122 follows the movement of bar 103. Means is also provided which is connected to conveyor belt 101 and amplifies the motion of bar 103 while causing movement of conveyor 101 in the desired direction. As illustrated, this means includes a closed linkage mechanism 124 including opposed parallel members pivotally connected with their ends to form a closed diamond. Mechanism 124 is pivotally connected at one apex 125 to a cross member 126 which is rigidly connected to cart 100, and is pivotally connected at the opposite apex 127 to conveyor belt 101. A cross member 128 is pivotally connected between opposite members of linkage mechanism 124, and cross member 128 is pivotally connected at an intermediate point 129 to cross member 122 at approximately its center. Thus, as cross member 122 is moved in conjunction with bar 103, moving pivot point 129 in the direction shown, linkage mechanism 124 is caused to move apex pivot point 127 with respect to apex pivot point 125, thus moving conveyor 101 with respect to cart 100. In FIG. 11, mechanism 124 is shown extended as it would be with the patient loaded in machine 30, and mechanism 124 is retracted with cross member 122 adjacent cross member 126 as shown in dotted lines when the patient is lying fully on cart 100. In the arrangement described, the relative movement of apex pivot point 127 with respect to apex pivot point 125 is greater than the movement of pivot point 129, for example 3–4 times depending on the relationship of the elements described, thus providing significant amplification of the movement of bar 103 in response to hydraulic cylinders 105, and reducing the stroke length requirement for the cylinders. The amount of amplification provided can be increased or decreased as desired by varying the size of linking mechanism 124, although it is desirable that linkage mechanism 124 not be so large that it extends beyond the sides of cart 100 when retracted. Conveyor belt 101 can be marked with the proper patient position so that full travel of piston rods 104 will carry him from the position of FIG. 8 to the position of FIG. 9.

PATIENT ELEVATOR LIMIT SWITCHES

During elevation and positioning of a patient in apparatus 30, care must be taken to avoid hitting the patient's head or headrest 41 against x-ray source 44. Also, care must be taken to ensure that the patient's head is properly positioned between source 44 and film holder 45 so that the patient is not struck by either of these objects when disc 42 is rotated. Further, it is highly desirable that the patient be fully withdrawn from apparatus 30 and fully on cart 100 before the cart is fully lowered to where it can be removed from elevator apparatus 33. In view of these requirements, it is preferred that certain limit switches be provided in association with elevator apparatus 33 and patient conveyor cart 100 to automatically limit the movement of the patient or disc 42 when the danger of interference is present. Examples of such limit switches which have been established to be desirable for this purpose are shown in FIGS. 9, 10, and 12. Of course, the number and location of such switches can vary depending on the degree to which the operator is to be entrusted to operate apparatus 30 within safe limits.

As shown in FIG. 10, one of tubular arms 107 includes a rectangular window 130 in it and an actuator plate 131 is mounted on telescoping arm 106 adjacent window 130 so that as arm 106 moves up and down, plate moves up and down in window 130. Also, a hollow tube 132 is mounted on lower plate 35b of platform 35 and extends through plate 108 to a position parallel to and adjacent arm 107 and window 130. A limit switch LS1, which can be connected to inhibit the operation of cylinders 110 and 112, is mounted on arm 107 adjacent the lower end of window 130 and includes a long actuator arm 133 extending down from it at an angle with respect to arm 107. Tube 132 includes an elongated slot 132a in its lower end, and a pin actuator 134, having a pin 134a extending through slot 132a, is slidably mounted in tube 132, and urged towards the bottom of tube 132 by a spring 135. A cable 136 is connected to pin actuator 134 and extends up through tube 132, about an amplifying idler wheel 136a (see FIG. 9) to the lower end of headrest 41 so that as headrest 41 is tilted about its pivot point, pin actuator 134 moves up and down in slot 132a to change the vertical position of pin 134a with respect to actuator arm 133. Wheel 136a functions to amplify the motion of the headrest. Also, as platform 35 moves up and down tube 132 moves up and down with it also changing the vertical position of pin 134a with respect to actuator arm 133. Thus, the actuation of arm 133 by pin 134a depends both on the amount of tilt of headrest 41 and the vertical position of elevator platform 35 so that when the headrest is up, the patient can be moved in to apparatus 30 with platform 35 at a lower position than is possible when the headrest is down and could strike x-ray source 44. The operating parameters of limit switch LS1 can be set to make sure that headrest 41 always clears source 44 at any elevation of platform 35. For example, if headrest 41 moves vertically up to 2 inches, and platform 35 moves vertically up to 8 inches, then arm 133 must be at least 10 inches long to cover the possible total vertical movement of 10 inches. The angle of arm 133 and length of pin 134a should be such that switch LS1 is actuated whenever source 44 would be struck by headrest 41 when moving inward.

However, when the patient is all the way out of x-ray apparatus, or out a sufficient distance that danger of hitting source 44 is not present, then a limit switch LS2, mounted in association with one of arms 109 (see FIG. 9) can be actuated to override switch LS1 and permit up and down movement of platform 35.

The vertical elevation of platform 35 can also be detected by limit switches LS3 and LS4 which are mounted adjacent window 130 so that they can be actuated by plate 131. Switch LS3 can be mounted at a position so that it can be utilized to sound an alarm when the elevation of platform 35 is such that with headrest 41 up, a normal sized head would be struck by film holder 45 during rotation about the front of the head. Switch LS4 can be mounted at a position so that it can be utilized to sound an alarm when the elevation of platform 35 and headrest 41 is such that the headrest 41 would be struck by film holder 45 during rotation about the back of the head. If desired, a vertical scale (not shown) can be provided to show the vertical position of platform 35 and red markings provided to indicate danger zones.

A limit switch LS5 is mounted adjacent window 130 to be engaged by plate 131 for interrupting the vertical down motion of elevator apparatus 33 when the front wheels of cart 100 are a fixed distance from the ground, for example ¼ inch, and permit the belt conveyor to be driven to its home position (all the way out). Another limit switch LS6 is mounted in platform 35 to sense when conveyor 101 is home and permit the completion of the vertical descent of elevator apparatus 33. Another limit switch LS7 may be mounted in platform 35 adjacent slot 40 so that it can be actuated by bar 102 when properly inserted and interrupt any elevating operation or operations of conveyor belt 101 until it is properly actuated.

Thus, with the conveying apparatus described, a patient can be safely and rapidly brought to the proper position in apparatus 30. Since his head rests firmly on headrest 41, the patient can relax and does not need to try to hold his head steady at an unnatural position. In adjusting the position of the patient's head in apparatus 30, the operator need only site the portion to be x-rayed in the line of sight of the x-rays, and adjust the elevation of the head to the proper distance from film holder 45 by use of tape means 47.

The electrical connections of the limit switches described and their function in controlling the application of power to the various solenoid valves of the patient elevating and conveying apparatus are shown in FIG. 20, and the hydraulic system is shown in FIG. 19. As shown in FIG. 9, the hydraulic system for operating cylinders 70, 105, 110, 112 and 115 can be mounted inside of pedestal 32 as represented by the dotted box 190. Referring to FIG. 19, this apparatus includes a hydraulic pump 191 connected between a low pressure inlet 192 to a source of hydraulic fluid generally represented by the number 193, and at its high pressure outlet 194 to a fluid distribution manifold 195 including a plurality of fluid inlets and outlets. The fluid return 196 from manifold 195 is connected to source 193 to establish a closed cycle fluid system. A controlled bypass 197 may be connected across conduits 194 and 196 to pump a portion of the fluid output of pump 191 into source 193 to reduce the flow rate of the pump under control.

Fluid inlets and fluid outlets of manifold 195 are connected to conduct fluid to and from a series of three position, four way, solenoid operated spool valves. In addition to valve 71, previously described, a solenoid operated valve 198 is provided for controlling cylinder 110, a solenoid valve 200 is provided for controlling cylinder 112, and a solenoid valve 201 is provided for controlling cylinder 115. Valves 71, 198 and 200 are identical as shown, and valves 199 and 201 are modified to permit use of pilot operated check valves 202 and 203, respectively, as shown in FIG. 19. Both cylinder 110, which controls the up and down motion of apparatus 33, and cylinder 115, which controls headrest 41, must hold a vertical load for a certain length of time, and pilot check valves 202 and 203 are provided to prevent fluid leakage or seepage which would otherwise cause the supported mechanism to slowly decline in elevation. In all other respects, the hydraulic system described is conventional.

Referring now to FIG. 20, the electrical switching is illustrated for operating solenoid valves 71, and 198–201. As shown, four double pole, double throw bat handle switches BS1, BS2, BS3, and BS4, which may be mounted on control panel 49 for operation by the operator, are illustrated as being connected at their pole terminal to line L1 providing a source of AC current along with line L2 which forms the AC common. Actuation of switches BS1–BS4 in one direction provides electrical current to the solenoid on one side of the respective solenoid valve, and actuation of the switches in the other direction provides current to the solenoid on the other side of the respective valve, thus effecting movement of the cylinders controlled thereby in both of their directions. As illustrated, switch BS1 is connected to supply power to lines Z4 and Y4 connected to the solenoid relays of valve 198 for controlling belt 101; switch BS2 is connected to supply power to lines Z2 and Y2 connected to the solenoid relays of valve 200 for controlling the in-out movement of elevator 33; switch BS3 is connected to supply power to lines Z3 and Y3 connected to the solenoid relays of lines Z1 and Y1 connected to the solenoid relays of valve 201 for controlling the angle of tilt of headrest 41. Limit switches LS1, LS2, LS5, LS6 and LS7 are also illustrated in FIG. 20 and are connected to interrupt the operation of the various solenoid valves when actuated. As illustrated, limit switches LS1 and LS2 are connected in series with the coil of an interference relay K7 so that the relay is actuated when an interference condition exists. Limit switch LS1 is normally open, and limit switch LS2 normally closed so that both switches LS1 and LS2 must be closed in order to permit relay K7 to be actuated. As noted, switch LS1 is closed when the inward movement of headrest 41 would cause it to strike source 44, and switch LS2 is closed when apparatus 33 is far enough out that this interference can't occur. Relay K7 includes terminal K7a which is connected to light an interference lamp 204 when actuated to provide a visual indication of an interference condition, and a contact K7b connected to switch A.C. power from line Z2 causing solenoid valve 200 to move the elevator in to line Z3 to cause solenoid valve 199 to be actuated to move the elevator up. Thus, when limit switch LS1 indicates interference during movement of elevator apparatus 33, and switch LS2 is not activated, the elevator apparatus is automatically caused to move upwardly until limit switch LS1 drops out when the interference condition is passed. Limit switches LS5 and LS6 are connected between switch BS3 and the elevator up-down solenoid valve 199 (line Y3) so that the downward motion of the elevator is stopped when limit switch LS5 is actuated, and until limit switch is actuated by conveyor belt 101 moving to its home position. Also relay K7 includes a contact K7c which is connected to switch the power on line Y3 normally operating solenoid valve 199 to move the elevator down, to the elevator in-out solenoid valve 200 (line Y2) to automatically move the elevator out when relay K7 is actuated until it is out a sufficient distance to avoid interference. As illustrated, limit switch LS7, which senses when the patient conveyor cart 100 is in position on platform 35, is connected in line Z4 between switch BS1 and solenoid valve 198, thus deactivating the belt in-out action until LS7 is actuated.

Also, as illustrated, limit switches LS3 and LS4 may be connected between a source of voltage and a suitable alarm (not shown) by contacts of a section F of a mode switch MS so that, for example, if two separate modes of operation of x-ray apparatus are employed, having different safe limits, limit switch LS3 is actuated in one mode and limit switch L4 is activated in the other mode.

THE FILM DRIVE MECHANISM

Referring now to FIGS. 13–17, a preferred form of film drive mechanism of this invention is illustrated for advancing the x-ray film as it is moved around the object being x-rayed. As illustrated in FIG. 13, a cylindrical film cassette 46 is utilized in the present apparatus for supporting a partially folded x-ray film 140 inside of an opaque, removable film pouch 141, and film cassette 46 is rotated to advance film 140 as disc 42 is rotated to provide a panoramic x-ray. If the object to be x-rayed were a perfect circle, then the speed of rotation of film cassette 46 would have to be equal to that of disc 42. However, during operation of x-ray apparatus 30, while x-raying through the skull, for example, the speed of rotation of film cassette 46 must, due to the configuration of the cross section of the skull, vary slightly from the speed of rotation of disc 42 in order to compensate for different circumferential speeds at different positions along a desired focal trough. In the past, such as in the Vertical Panorex apparatus maufactured and sold by the assignee of the present invention, this slight variation in film speed has been provided by utilization of a basis cam 142 shown in FIG. 14a which includes lobe portions which closely follow the contour of the skull. During operation of that machine, the drive mechanism for driving the x-ray source is directly coupled to the basic cam 142 which is, in turn, coupled to drive an x-ray film, mounted in a flat film holder, past a slot at a speed which is proportional to the shape of the cam. However, this direct drive mechanism requires mechanical linkage by thin wire and is subject to mechanical problems and film jitter, and an important feature of the present invention is the provision of a drive mechanism for moving the x-ray film at the required speed while moving disc 42, which employs no mechanical linkage between the drive mechanisms.

In x-ray apparatus 30, disc 42 may be driven by motor 63 at a constant speed of 2 rpm and the film speed mechanism of this invention to be described permits programmed speed variations in a 2 rpm motor utilized to drive film cassette 46 in order to synchronize the film speed to the circumferential speed of the outline of the object being x-rayed which, as noted, is other than a perfect circle.

In a constant speed motor, the effective output revolution is the shaft rotation with respect to its stator, normally a stationary housing. Conversely, if the housing is allowed to rotate, its speed would increase or reduce the differential speed between the rotating shaft and an external fixed base, depending on the direction of movement of the housing with respect to direction of rotation of the rotating shaft. The present invention uses this technique to satisfy the requirements of a variable speed film drive which is accurately responsive to speed variation of fractional revolutions without introducing jitter. To accomplish this, basic cam 142 is redesigned utilizing variations in the radius of the basic cam to provide a sloped cam 143 illustrated in FIG. 14B. Whereas the basic cam shape closely follows the shape of the desired focal trough, and its circumferential speed at any excursion point is the desired film speed, the sloped cam must provide for differentials in radius at adjacent excursion positions proportional to the required change in film speed. To accomplish this, the change in radius of the basic cam between adjacent excursion positions (for example, 15° apart) is determined and converted directly to a plus or minus change in rotational speed between adjacent 15° positions to provide a required change in slope for the translated cam. In starting with a basic radius for sloped cam 143, then the change in slope can be translated into a minus or a positive increase or decrease in radius of the new cam to provide the desired slope.

In order to utilize sloped cam 143 as a mechanism for varying the speed of the film drive motor, means is provided by the present invention for rotating the housing of the motor in response to change in slope of the sloped cam as the cam and the shaft of the motor are rotated in synchronism. In this manner, the motor shaft, which can be coupled to drive cylindrical film cassette 46 will have a variable speed with respect to the motor housing as determined by the slope of the cam of FIG. 14B.

Figure 15:
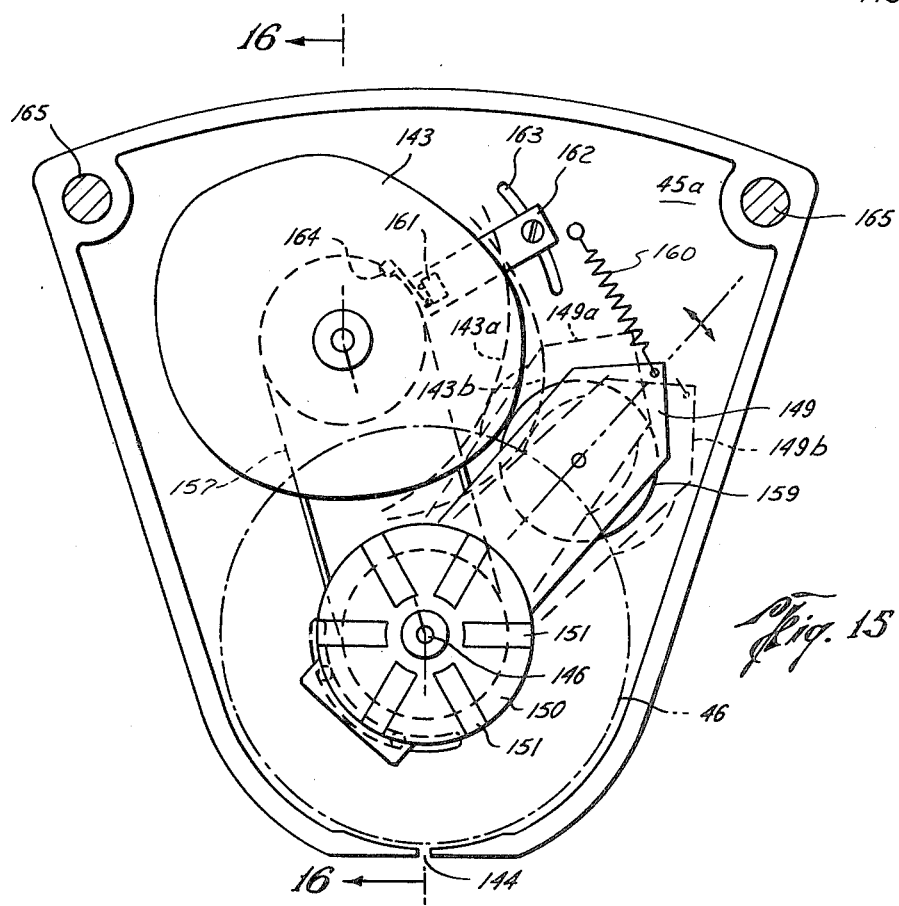
FIG. 15 is a front view in elevation of the film drive mechanism of the present invention shown without the film holder in place.

The film drive means utilizing the concept is illustrated in FIGS. 15–17.

Film cassette 46 and the drive mechanism therefor are mounted inside housing 45 which includes an x-ray slit 144 in its lower portion as shown in FIG. 15, x-ray slit 144 being aligned with an x-ray beam from x-ray source 44. Thus, as film cassette 46 is rotated to rotate unexposed x-ray film 140 past slit 144, film 140 is exposed to the x-rays in the conventional manner. As show in FIG. 16, a constant speed electric motor 145 having an output shaft 146 may be connected to a suitable bushing 147 mounted on the rear plate 45a of film holder housing 45 so that shaft 146, or an extension thereof, extends through an opening in plate 45a. The housing of motor 145 is free floating as hereinafter described. Shaft 146 extends inside housing 45 to support a pulley 148, a motor housing lever arm 149, and a magnetic clutch mechanism 150, having spaced permanent magnets 151 on it (see FIG. 15). Cylindrical film cassette 46 includes a metal plate 152 located on the rear thereof so that film cassette 46 may be mounted on clutch 150 and supported thereon for rotation by force of magnets 152, and yet be easily removed when required. A guide rod 153 may be provided at the center of clutch 150 which fits in an opening in the center of the rear plate of film cassette 46, to properly position film cassette 46 on clutch 150, and film cassette 46 may include a central handle 154 extending from the center of its bottom plate, for aiding in placing and removing film cassette 46 on magnetic clutch 150. Thus, with the apparatus described, as motor 145 rotates it functions to rotate film cassette 46 at the speed of rotation of shaft 146.

Cam 143 is rotatably mounted on the rear plate 45a of housing 45 by a shaft 155 on which a pulley 156 is mounted. A timing belt 157 is connected between pulleys 148 and 156 so that these pulleys and sloped cam 143 rotate in synchronism with shaft 146 as motor 145 is operated. However, the housing of motor 145 is connected by a pair of rods 158 through a slotted opening 158a in rear plate 45a, and rods 158 are rigidly connected to an end of a lever arm plate 149. As illustrated in FIG. 15, lever arm 149 is pivotally mounted intermediate its ends about shaft 146 so that it can pivot with respect to the shaft, and a cam follower idler wheel 159 is mounted at the end of lever arm 149 opposite the end to which rods 158 are connected, for following the rotation of sloped cam 143. A spring 160 is connected between the end of lever arm 149 on which idler wheel 159 is mounted and the backwall 45a of housing 45 so that idler wheel 159 is resiliently urged against sloped cam 143 as the cam is rotated. Since lever arm 149 is free to pivot about shaft 146, and since the housing of motor 145 is rigidly connected through rods 158 to the opposite end of lever arm 149, as lever arm 149 pivots about shaft 146 between the dotted line positions 149a and 149b shown in FIG. 15, the housing of motor 145 rotates with respect to shaft 146 to increase or decrease the relative rotational speed of the shaft. As illustrated in FIG. 15, when cam 143 is at its minimum diameter 143a at the point where it is engaged by idler wheel 159, plate 149 is in the dotted line position 149a, and when cam 143 is at its maximum diameter 143b at the point where it is engaged by idler wheel 159, plate 149 is in the position 149b.

In order to control the rotation of film cassette 46 and cam 143, a microswitch 161 is mounted on a plate 162 extending between shaft 155 and a slotted opening 163 in wall 45a. A notch 164 may be provided in pulley 156 so that the contact arm of switch 161 moves in and out of the notch as pulley 156 is rotated. The operation of switch 160 in controlling the operation of motor 145 is described with reference to FIG. 22.

By mounting plate 161 in the manner shown in FIG. 17, it can be pivoted about shaft 155 to adjust the position of switch 161 with respect to notch 164 when film cassette 46 is at a desired stopping position. Suitable distinctive marks may be provided on film cassette 46 and on housing 45 for ensuring that the operator properly orientates the film cassette when it is installed.

Also, a friction brake (not shown) can be provided on shaft 155 to place a constant drag on the rotation of shaft 146 to reduce the chances of backlash or jitter.

With the arrangement described utilizing sloped cam 143, the direction of the slope of the cam is responsible for an increase or decrease in the speed of rotation of shaft 146, while the degree of the slope is responsible for the magnitude of the speed variation as the shaft rotates. The range of speed variation is limited by the physical size of the sloped cam and the cam follower wheel 159. By use of a maximum 6 inches diameter cam, speed variations up to plus or minus thirty percent can be provided, if required.

Also, it is preferred that film holder 45 be slidably mounted on two spaced apart rods 165 mounted on disc 42 so that film holder can be moved between and positioned at the dotted and solid line positions shown in FIG. 9.

ELECTRICAL AND HYDRAULIC CIRCUITRY

Figure 21:
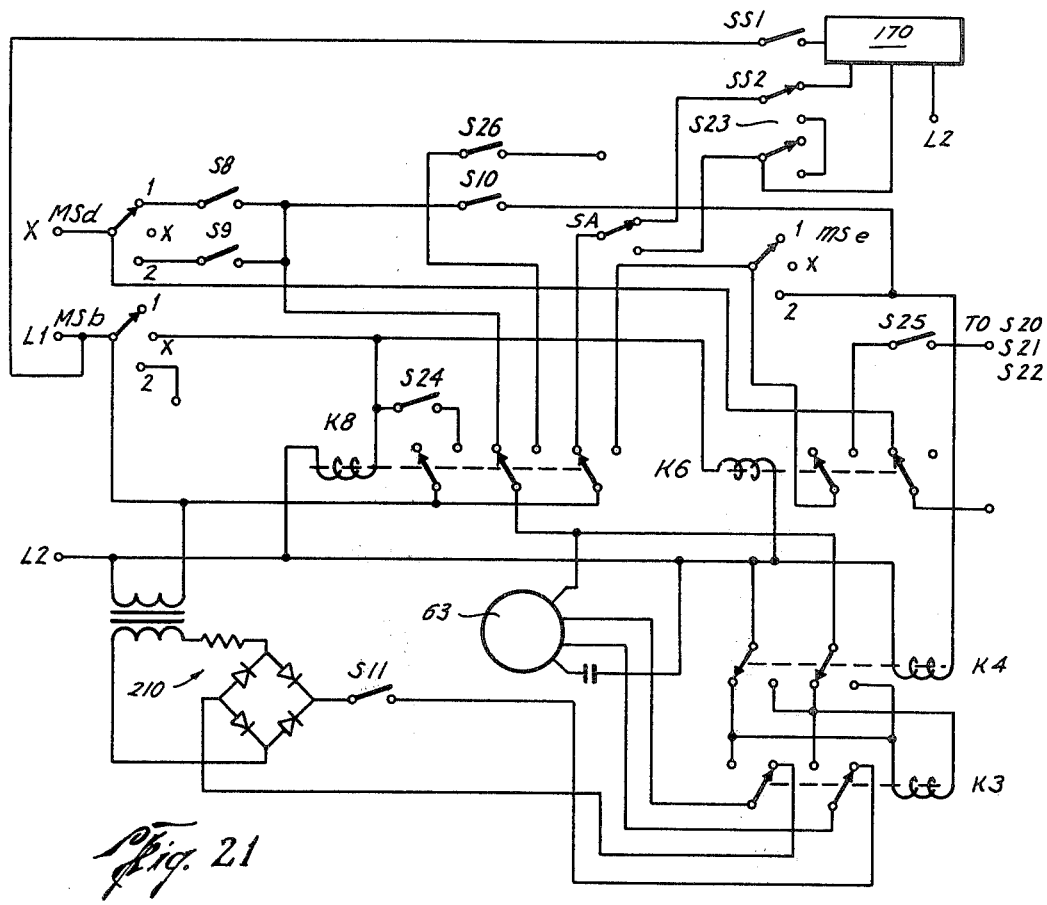
FIG. 21 is an electrical schematic of the switching apparatus for controlling the excursion of the x-ray source.
Figure 22:
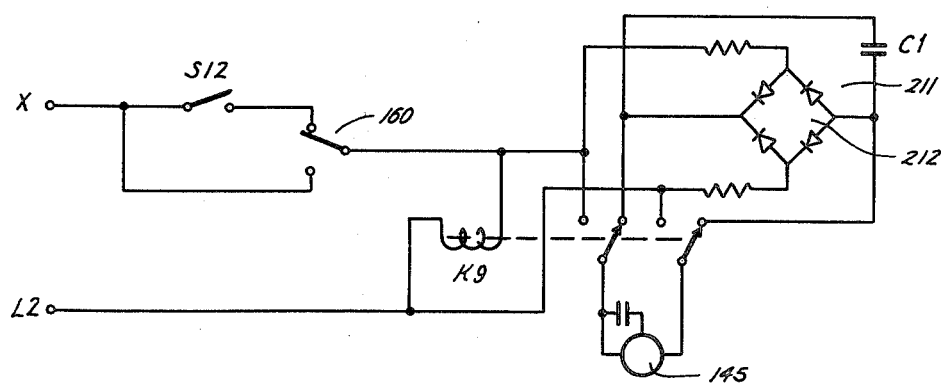
FIG. 22 is an electrical schematic of the switching apparatus for controlling the motion of the film cassette.

Referring now to FIGS. 18–22, the electrical and hydraulic circuitry for controlling the operation of x-ray apparatus 30 is illustrated. FIG. 18 illustrates a block diagram of the overall electrical system of apparatus 30 and the heart of this system is a multi-position, multi-step programmer 170 which is stepped between its respective steps by a stepper motor 171. Programmer 170 controls the sequence of operation of the various components of apparatus 30 in response to an operator command and automates this operation as much as possible to avoid the necessity of operator intervention in any desired sequence of operations. In the example shown of the present invention, prorammer 170 has at least 26 separate switching positions, each of which may be programmed to be either an open circuit or closed circuit in one or more of a series of 60 consecutive steps from a home position back to the home position, representing a complete cycle of a programmer. In addition to the programmer, the electrical control circuitry of FIG. 18 includes a remote control circuit 172 which permits the operator to remotely control the operation of the x-ray apparatus without being exposed to high voltage x-rays, and x-ray circuits for 173 for controlling the application of high voltage to x-ray source 44. As illustrated in FIG. 18, switch positions 1, 2, 4, 5, 6 and 7 of programmer 170 may be utilized to control the sequence of operation of the x-ray circuits 173 as the programmer moves between its sequential steps. Also, a disc drive and camera shift circuitry 174 is connected to positions 8, 9, 10, 24 25 and 26 of programmer 170 for controlling the rotation and direction of movement of disc 42, and the orientation of source 44 during various steps of the x-ray cycle and during the different modes of operation. Details of a preferred form of circuitry 174 are illustrated in FIG. 21. Position 11 of programmer 170 may be used to control the application of an electrical brake 175a provided from a D.C. source 175b to motor 63 for stopping the rotation of disc 42 at a desired position. A film cam drive circuit 176, illustrated in detail in FIG. 22, is connected to programmer switch 12, and programmer switches 13-19 are connected to the gimbal shift control circuitry 177, illustrated in detail in FIG. 20, for controlling shifting of gimbal frame 50. Switch positions 20-23 of programmer 170 are utilized to control the sequence of operation of a control circuit and mode switch (shown in FIGS. 20 and 21 by the reference MS) which in turn controls the operation of programmer 170 and the mode of operation of x-ray apparatus 30.

In a preferred form of x-ray apparatus described, two modes of operation are provided, referred to herein as mode 1 and mode 2. Mode 1 represents the operation of x-ray apparatus in x-raying the frontal portion of the head or skull, including the dental arch, whereas mode 2 represents application of the x-ray apparatus 30 to x-raying the back portion of the skull. The operation and structure of the present invention is shown and described herein as in mode 1 except as otherwise noted. Thus, by the provision of these two modes of operation, along with the ability to adjust the position of the subject being x-rayed in the machine and select a desired shift within the limits described tomographs of a desired portion or adjacent portions of the skull can be readily provided by the apparatus of this invention. The principles utilized by the invention to accomplish this can also be readily adapted to providing tomographs of other selected portions of the human body.

As a matter of convenience, and in order to establish the sequence of operation for a programmer 170 and the apparatus of this invention, switch positions 1-27 can be utilized for mode 1 operation with position 60 being the home position, and switch positions 28-54 can be utilized for mode 2 operation, again with step 60 as a home position. Positions 55-59 are not used except that position 59 may provide an event signal signalling that one more step is required to move the programmer to home position 60. An event signal is provided by switch position 3 on programmer 170 to operate an event counter which keeps count of the programmer cycles. In the following description and in FIGS. 20-22 each of the switch positions of programmer 170 is represented by the letter S followed by the number of the switch position.

Also, L1 represents one side of an A.C. input voltage, L2 the other side (or common), and X represents switched voltage L1, which may be provided by a push button remote switch permitting the operator to operate apparatus 30 from behind a protective shield.

Programmer 170 may include an internal control relay (not shown) and an external micro-switch SS1 which is actuated mechanically each step to ensure that the programmer has made a complete step. In the preferred embodiment of this invention illustrated switch positions 20-23 may be utilized to control the stepping of programmer 170. Also, a micro-switch SA may be mounted on frame 50 adjacent the top of disc 42 (see FIG. 2) and switch actuators may be located at the −9°, −60°, −120°, +9°, +60° and +120° positions of disc 42 for actuating switch SA, which is connected to ensure the full stepping of programmer 170 when actuated. The relationship of the positions of the switch actuator or disc 42 to the operation of apparatus 30 is explained with reference to the description of FIGS. 23A, 23B, 24A and 24B.

The manner in which shift selector switch 88 controls shift solenoid 71, through lines Z5 and Y5 is also illustrated in FIG. 20. Switch 88 is shown as a rotary switch having three sections, 88a, 88b, and 88c, each with positions 1-15 corresponding to the position of knob 89. Micro-switches 78b, 82 and 83 are connected in series between a source of electrical current (lines X and L2) and the solenoid coils of solenoid valves 71, and are shunted by programmer switches S18, S17 and S19, respectively, so that the programmer can selectively override the action of the micro-switches to cause a shift limit to be passed. Programmer switches S13 and S14 are also connected to the circuit through a section of a mode switch MS to switch power to the shift circuit during either mode 1 or mode 2 of operation, and the duration of shift is controlled by programmer switches S15 and S16 which switch the current to either section 88a or 88b of switch 88 to in turn control which of llines Z5 or Y5 is actuated. During any shifting operation of frame 50 of x-ray apparatus 30, it is preferrd that the high voltage to source 44 be cut off, and programmer switch S7 provides this function. Section 88c of switch 88 is used to shunt programmer switch S7 to override the cut off of the x-ray source when no shift is selected by the operator (i.e., knob 89 is set at the mid position 8).

Referring now to FIG. 21, wherein the control circuitry for excursion motor 63 is illustrated, the direction, movement, and braking of motor 63 are provided by relays K3, K4, K6 and K8. Relay K3 is connected to conduct D.C. voltage from a conventional A.C. to D.C. power supply 210 to apply a D.C. brake to motor 63 when switch contact S11 of programmer 170 is actuated. Relay K4 is connected to reverse the polarity of the line voltage driving motor 63 when switch contact S10 of programmer 170 is actuated. Relay K8 functions as a camera shift relay which is latched by one of its terminals and switch S24 to control the shifting of disc 42 between the respective starting positions in the two modes of operation. Relay K6 enables control switch S25 of programmer 170 which permits selected shifting of the camera during selected steps of the program. The function of these relays and their associated switches are explained with respect to the description to follow of the operation of apparatus 30 in FIG. 23A, 23B, 24A and 24B.

Referring now to FIG. 22, the preferred form of control circuitry for operating film drive motor 145 is illustrated. A double pole, double throw relay K9 is provided and this relay switches the input terminals of motor 145 between a source of running current between lines X and L2 and a capacitor brake illustrated generally by the numeral 211. Programmer switch S12 is in series with the control voltage of motor 145, as is limit switch 161 which is mounted on plate 162 to be actuated by pulley 156 as shown in FIG. 17. Switch 161 is shown in FIG. 22 in the position it is in when its actuator arm is in notch 164. Thus to start the movement of motor 145 with switch 161 in this position, it is necessary for programmer 170 to move to a position where switch S12 is closed. This causes relay K9 to switch to actuate motor 145 which, in turn, causes notch 164 to move away from the actuator of switch 161, thus closing switch 161 to continue to operate motor 145. Motor 145 runs until a complete cycle is completed (i.e., the film is fully exposed) at which time the actuator arm of switch 161 again drops in notch 164, releasing relay K9 to apply a D.C. braking voltage to motor 145. As illustrated, brake 211 includes bridge rectifier 212 for converting voltage between lines X and L2 to a D.C. voltage, and a capacitor C1 connected across bridge rectifier 212 and to motor 145 when relay K9 is released. Thus, during operation of motor 145, capacitor C1 is charged and this charge is utilized to apply a braking current to motor 145 to cause it to accurately stop each time a complete cycle of rotation for film cassette 46 is provided, or if excursion is to be stopped at will at any time during the excursion.

OPERATION OF THE X-RAY APPARATUS

Referring now to FIGS. 2, 23A, 23B, 24A and 24B, operation of x-ray apparatus 30 will be explained with reference to the two mode of operation provided by the preferred embodiment illustrated. In this description it is assumed that patient P has been properly positioned in x-ray apparatus 30 for the start of operation in the selected mode and that the desired gimbal shift for frame 50 has been selected, and that only initiation of a cycle start button (generally a remote pushbotton, dead man type switch) is required.

In positioning the head of the patient in the dental mode a clear plastic, L-shaped guide plate 250, with lines 251 on it at about 20° with respect to the vertical may be placed against film holder 45 is shown in FIG. 9 to permit the inferior border of the mandible to be lined up with one of lines 251. This ensures that the dental arch will be x-rayed without projecting x-rays through bone structure that would cast shadows on the image.

Also, reference herein to the angular position of the disc 42 refers to the angular positions shown in FIG. 2. At the start of any cycle of operation in mode 1, programmer 170 is in its home position 60 so that the next adjacent position of the programmer is step position 1. Also, in this position of the programmer, by completion of a previous cycle disc 42 has automatically been driven to position where source 44 and film holder 45 are in line with vertical centerline CL (the solid line position of source 44 and film holder 45 in FIG. 2). In response to an operator command, such as by actuation of an "initiate" switch, programmer 170 is caused to move from its home position to step position 1, the start of mode 1. By energizing a remote pushbutton switch, the mode 1 cycle begins at which time the programmer switches 8 and 10 are actuated for driving the excursion motor in the counterclockwise direction to move the film holder 45 and source 44 to the solid line position shown in FIG. 23A where film holder 45 is at −120°, while film 140 is started to rotate in holder 45 past slot 144. Also, since the cycle started with frame 50 at the 0° shift position, programmer switch S13, which activates the gimbal shift in mode 1, and programmer switch S15 which causes the shift to move in a clockwise direction, are actuated along with programmer switch S18 bypassing center limit switch 78b. Also, actuation of shift control switch S13 (S14 in mode 2) supplied power to line W (FIG. 20) interrupting fluid bypass 197 so that shift cylinder 70 is operated at a higher speed than the rate of the other cylinders. This causes cylinder 70 to move frame 50 for one-half of the full amount of the selected shift so that its vertical centerline is now located at line CL' in FIG. 23A. This shift is disabled as film holder 45 reaches the −9° position (FIG. 2) where microswitch SA is actuated to cause programmer 170 to step from positions 1 to 2. The disc excursion continues to move film holder 45 through the −60° position (FIG. 2) to the −120° position shown in solid lines in FIG. 23A where the counterclockwise motion of the disc is stopped, and the x-ray source filament is turned on by a programmer switch S5. Programmer 170 automatically steps to the next step portion 5 and programmer switch S10 is released to change the polarity of the excursion drive motor to cause rotation of disc 42 in a clockwise direction. The programmer goes through steps 6, 7 and 8 and at step 8, the clockwise run of disc 42 is started by again actuating programmer switch 8 and turning on the high voltage (done at stepper position 9 by programmer switch S7) to start the x-ray cycle. Film holder 45 moves from the −120° to position through the −60° position to the −9° position during stepper positions 9–11, at which time the high voltage to the x-ray is cut off by releasing programmer switch S7, and the full shift of gimbal frame 50 is initiated by actuation of programmer switches S13 and S16. Limit bypass switches S18 and S19 are actuated during this step so that switch actuator 78 moves from right limit switch 83 to left limit switch 82, which has not been bypassed, at which time the shift is cut off. Thus, the positions of switches 82 and 83 with respect to each other determines the extent of the shift. When this shift occurs, frame 50, x-ray source 44 and film holder 45 are moved to the solid line positions shown in FIG. 23B, where the vertical centerline of frame 50 is indicated as being the line CL''. During shifting the excursion motor is kept running so that film holder 45 passes through the 0° position of FIG. 2, and when the +9° position is reached, the x-ray high voltage source is again turned on by actuation of programmer switch S7. As the programmer steps from step positions 12 to 14, film holder 45 moves respectively through the +60° and to the +120° position. At stepper position 14, the high voltage and filament to x-ray source 44 is cut off by deactivating programmer switches S4, S5 and S7, and the clockwise excursion of disc 42 is disengaged. In steps 15 through 18 of the programmer, the polarity of the A.C. driving of excursion motor 63 is reversed, and in stepper positions 19 and 20 the excursion motor is driven back in a counterclockwise direction until film holder 45 reaches the +9° position at which time the left limit bypass provided by programmer switch S17 is activated, and the center line switch 78b bypass provided by programmer switch S18 is removed, permitting a one-half shift of frame 50 back to its original starting position. Positions 22 through 26 of stepper are utilized to stop the excursion of disc 42 and the shift and to set the apparatus for the start of the next cycle. Step positions 26 and 27 are utilized to automatically step programmer under control of programmer switch S21 to the home position 60 as soon as the remote pushbutton switch is released.

Thus, as illustrated in FIGS. 23A and 23B, a panoramic radiograph of the front portion of the head of patient P may be provided, with a first half section being x-rayed by rotating disc 42 120° about one center of rotation C', and a second half being x-rayed by rotating disc 42 120° about another center of rotaton C''. FIG. 25 illustrates an example of such a radiograph taken in mode 1 through the dental arch. The center, unexposed area 140a represents the movement of film 140 and disc 42 through the —9° to +9° excursion described.

FIGS. 24A and 24B illustrate the sequence of operation of apparatus 30 in mode 2 wherein the back of the head of patient P is x-rayed. As noted, stepper positions 28 through 54 are utilized for mode 2 operation and at the start of the mode 2 cycle film holder 45 must be shifted to the —60° position in order to permit proper placement of the patient in the apparatus so as disc 42 rotates to the start position, the patient's head will not be struck. This placement is different in mode 2 because in this mode the film holder 45 passes round the back of the head of the patient and the x-ray source 44 passes about the front of the head. For sake of convenience, when mode switch MS is switched to mode 2, and prior to the mode 2 run, programmer 170 can be caused to run the excursion motor in a counterclockwise motion until film holder 45 is just prior to the —60° position. At this time film holder 45 will be in a start mode 2 position and the patient may be loaded into the apparatus. At the initiation of the mode 2 cycle, programmer 170 will step to position 28, the start of mode 2. Energizing the remote pushbutton switch will cause disc 42 to rotate in the counterclockwise direction to move x-ray source 44 and film holder 45 to the dotted line position shown in FIG. 24A where film holder 45 is at the +60° position which is the position at which the x-raying of the back of the head begins. During this rotation of disc 42 which is controlled by stepper positions 18–38, when film holder 45 passes from the —171° position to the+171° position, one-half of the alloted shift for frame 50 is provided to move line CL to CL' as shown in FIG. 24A. When the +60° position for film holder 45 is reached, the polarity of excursion motor 63 is reversed at stepper position 39, the x-ray source turned on, and disc 42 is rotated clockwise to move film holder 45 back past the +171° and —171° positions, between which the full shift of gimbal frame is provided (at the solid line position of FIG. 24A) moving centerline CL from line CL' to line CL'' as shown in FIG. 24B. Again, the high voltage source is disabled at the +171° position of film holder 45 and enabled again at the —171° position of film holder 45 so that no x-rays are provided as the apparatus passes about the center of its rotation, generally at a time when the spinal cord of the patient would be in line with the x-rays.

As shown in FIG. 24B, after shifting, source 44 and film holder 45 (now in the dotted line position) move in the clockwise direction to the solid line position shown for x-raying the last half of the portion of the skull being x-rayed. When the solid line position of FIG. 24B is reached, represented by return of film holder 45 to the —60° position, the x-ray source is cut off and disc 42 is automatically caused by programmer 170 to move to its home position as programmer 170 moves to home position 60 after the remote pushbotton switch is released. This is to prepare x-ray apparatus 30 for the start of another cycle of operation. Also, the one-half shift is initiated to bring line CL back to its starting position at vertical dead center.

In both mode 1 and mode 2, at the time that the cycle is initially turned on, programmer switch 12 is actuated to bypass microswitch 161 and start the rotating of film 140 and this rotation continues at least for the time during the x-ray scan when source 44 is on, but generally longer as shown by the unexposed portions of the film on either side of the exposed portions. The position of switch 161 with respect to notch 164 can be adjusted to cause the movement of film 140 to stop upon completion of a full cycle of operation.

Of course, the sequence of operation of the various components of x-ray apparatus 30, and the various positions of disc 42, source 44, and film holder 45 can be varied as required for a specific x-ray operation. However, with the two modes of operation described, x-ray can be provided of both the front portion of the patient's skull, including the dental arch, and of the back portion with appropriate shift provided for providing a desired focal trough or avoiding the passage of x-rays through the patient's spinal cord, or other objects which would provide shadows that decrease the clearness of the x-rays. As shown in FIG. 9, by the dotted line positions for x-ray source 44 and film holder 45, the line of sight of source 44 and holder 45 with respect to each other can be changed during the different modes of operation to direct the x-ray beams through a desired portion of the skull, once the position of headrest 41 is set (which, of course, can also be adjusted). As noted in FIG. 9, x-ray source 44 may be mounted to swivel on a bracket 44a, and the solid line position shown represents orientation of x-ray source 44 at a 7° angle with respect to vertical. This position, which is suitable for x-raying a dental arch, requires that film holder 45 be located in the solid line position shown. For mode 2 operation, where the back of the head is being x-rayed, x-ray source 44 can be positioned in the vertical dotted line position, and film holder 45 positioned in the outer dotted line position as illustrated in FIG. 9.

Also, while the x-ray source is normally cut off during shifting of frame 50, when selector switch 88 is in position 8 and no shift is provided, programmer switch S7 can be actuated to bypass the x-ray cut off function and provide a continuous x-ray without the unexposed center area 140a.

An important feature of the present invention is that adjustments by the operator to properly set the apparatus for a desired operation are minimized. In the usual situation, other than setting the orientation of the x-ray source with respect to vertical and positioning of film holder 45, which settings may remain fixed through a large number of x-raying operations, the operator needs only to dial in the direction and amount of shift for frame 50 and orientate and position the patient's head at the correct object-to-film distance, by use of tape measure 47.

With reference to FIG. 2, position 8 on scale 90 represents zero shift of frame 50; positions 1–7 represent negative shifts in one-half centimeter increments where the left half (0° to —120° ) of the rotational scan is taken from a shifted center of rotation C'' (shown at the extreme negative shift provided at position 1 for knob 89); and positions 9–15 represent positive shifts in one-half centimeter increments where the left half of the rotational scan is taken from shifted center of rotation C' and the right half scan is taken from shifted center of rotation C'' (shown at the extreme positive shift provided at position 15 for knob 89). FIGS. 26–28 illustrate the manner in which the proper shift may be provided to obtain the best line of focus of a portion of the skull to be radiographed. In FIG. 26, a preferred form of a slide rule profile projector 220 is illustrated which includes two members 221 and 222 mounted in any suitable manner to slide with respect to each other, such as by a pin and slot arrangement. Members 221 and 222 may be made of transparent plastic and one of the members includes a scale 223 on it which is numbered from 1 to 15 (corresponding to the numbers of knob 89 and scale 90) and the other member includes an arrow 224 on it which is adapted to move along scale 223 as members 221 and 222 slide with respect to each other. For example, in the preferred embodiment illustrated of projector 220, member 222 can be moved back and forth on member 221. As illustrated in FIG. 26, member 221 includes an arcuate section 221a which is shaped generally to conform with the outline of a cross section through the left half of the skull of a human, particularly through the dental arch. A similar arcuate section 222a is provided on section 222 for the right half skull cross section. These curved sections are similar to the curved faces of basic cam 142 since they represent the actual line of focus of apparatus 30. Thus, as illustrated in FIG. 27, wherein a cross section of a human skull is illustrated through the dental arch, with the spine S shown in the approximate center thereof, slide rule profile projector 220 can be overlayed on the cross section with arcuate section 221a located along the left side of the dental arch and arcuate section 222a located along the right section of the dental arch. When this is done, the position of arrow 224 with respect to scale 223 can be read on scale 223, for example, between positions 5 and 6 as shown in FIG. 26, representing a negative shift of the center of rotation C from position C' to position C''. Switch selector switch 88 can be correlated with these readings in a manner so that by selecting switch position 6 on knob 89 the required shift for providing the full x-ray of the dental arch shown in FIG. 27 can be provided. Because of the relatively wide focal trough 225 and 226 provided (represented by the dotted lines in FIG. 27) and the overlap between the left half and right half scans, the shift of frame 50 does not have to be precise and ½ to 1 cm. steps between shift provides satisfactory resolution. By appropriate selection of the center of rotation of disc 42, a slight overlap between the left side and right side x-ray scans or radiograph 140 can be provided so that a full picture of the dental arch is illustrated.

FIG. 28 represents the use of projector 220 to determine the setting for knob 89 to x-ray selected portions of the lower portion of a skull, represented in cross section in FIG. 28. As shown, a positive shift sufficient to move center of rotation C from position C' to C'' is indicated by scale position 10.4, or position 10 for knob 89.

Thus, the best line of focus outline can be determined with projector 220 by sliding arrow 224 on movable portion 222 toward a greater position number on scale 223 (9–15) for an increasing focal diameter, or toward a smaller number on scale 223 (1–7) for a decreasing focal diameter. The curved outlines 221a and 222a represent, in either case, the resulting line of best focus. The center gap, at a position for arrow 224 greater than 8, indicates the area missed by the radiograph. Conversely, the center overlap of the two curved sections represents the object overlap on position numbers smaller than 8 when the corresponding shift number is dialed into the shaft selector switch 88. A center white stripe will show on the radiograph as a result of the x-ray cutoff during shift, except during no shift position 8.

Also, as shown in FIG. 26, a ruler 230 scaled, for example, in centimeters (assuming that tape measure 47 is similarly scaled) may be mounted on projector 220 for determining the correct object-to-film distance when positioning the head of the patient in apparatus 30. As shown in FIGS. 27 and 28, this distance would be about 8½ cm. when projector 220 is overlayed on the skull cross sections illustrated. Persons with a larger or smaller head would provide different readings. The reading on ruler 230 can be read on tape measure 47 to set the distance to the outer extremity of the portion of the skull from slit 144 in film holder 45.

The skull dimensions of the patient for determining the size of the skull cross section section shown in FIGS. 27 and 28 can be readily determined in a conventional manner by the radiologist or technician.

As illustrated in FIGS. 27 and 26 by focal troughs 225 and 226, and in FIG. 26 by a representative radiograph actually provided by use of an x-ray apparatus constructed in accordance with this invention, the resulting radiographs from this invention are provided of a continuous curved plane having a depth of focus of, for example, ½ cm. Thus, a zone of focus suitable for tomography and zone laminography is provided to provide a definitive picture of the examined area. By offsetting successive radiographs at, for example, in ½ cm. steps, on either side of an area being examined, the effective depth of focus can be increased and a three dimensional picture of the examined area can be provided to improve the diagnostic use of the radiographs.

Also, while in the embodiment illustrated, the best line of focus is represented by curved section 221a and 222a, which are determined by the configuration of sloped cam 143 (which is, in turn, determined by the configuration of basic cam 142), different configurations of cam 143 can be used and corresponding different lines of focus provided by proper shaping of sections 221a and 222a. This is accomplished again by translating the shape of a basic cam corresponding to desired lines of focus to the required sloped cam shape as heretofore explained.

Thus, by providing effective means for changing the shape of the focal trough, by providing for changing the width of the focal trough by selecting different shifts for gimbal frame 50, and by providing for relatively easy selection of different orientations of the object being examined and the object-to-film distance, a highly versatile x-ray apparatus with a wide range of capability for medical and dental application is provided. Further, by the use of an automated programmer and automatic limit switching during patient placement and positioning, the chances of operator error or misjudgment are greatly reduced. The capabilities of the x-ray apparatus of this invention compare very favorably with x-ray apparatus that are a good deal more complex and many times more expensive.

From the foregoing, it will be seen that this invention is one well adapted to attain all of the ends and objects hereinabove set forth, together with other advantages which are obvious and which are inherent to the apparatus.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

What is claimed is:

1. A conveyor cart for aiding in the placement of a subject to be x-rayed or treated in position in a radiographic apparatus, comprising, in combination:
    an elongated frame;
    a conveyor belt mounted on said frame and along the length thereof to move a subject placed on said belt along the length on said cart from a first position where said subject can be placed on said cart to a second position on said cart where he can be positioned in said radiographic apparatus; and
    coupling means mounted on said frame and connected to said belt and adapted to be actuated by a movable element in said radiograhic apparatus for moving said belt, and means connected between said coupling means and said conveyor belt for amplifying the motion of such a movable element to cause a greater movement of said belt in response thereto.

2. The conveyor cart of claim 1 wherein said amplifying means includes a closed linkage mechanism having opposed parallel members pivotally connected together at their ends to form a parallelogram, the junction of two of said members being pivotally connected to said coupling means and responsive to movement thereof and the junction of two other of said members being pivotally connected to said conveyor belt so that relative movment of said junction towards and away from each other causes movement of said belt.

3. The conveyor cart of claim 2 wherein the relative movement of said conveyor belt in response to movement of said coupling means is at least three times the relative movement of said coupling means.

* * * * *